(12) United States Patent
Safo et al.

(10) Patent No.: US 10,875,834 B2
(45) Date of Patent: Dec. 29, 2020

(54) PRODRUG AND PROTECTED FORMS OF 5-HYDROXYMETHYLFURFURANAL (5-HMF) AND ITS DERIVATIVES

(71) Applicant: VIRGINIA COMMONWEALTH UNIVERSITY, Richmond, VA (US)

(72) Inventors: Martin K. Safo, Richmond, VA (US); Guoyan Xu, Richmond, VA (US); Yan Zhang, Richmond, VA (US); Osheiza Abdulmalik, Richmond, VA (US)

(73) Assignees: Virginia Commonwealth University, Richmond, VA (US); The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 16/318,590

(22) PCT Filed: Jul. 24, 2017

(86) PCT No.: PCT/US2017/043475
§ 371 (c)(1),
(2) Date: Jan. 17, 2019

(87) PCT Pub. No.: WO2018/018035
PCT Pub. Date: Jan. 25, 2018

(65) Prior Publication Data
US 2019/0256483 A1  Aug. 22, 2019

Related U.S. Application Data

(60) Provisional application No. 62/366,250, filed on Jul. 25, 2016, provisional application No. 62/365,563, filed on Jul. 22, 2016.

(51) Int. Cl.
*C07D 307/46* (2006.01)
*A61P 7/00* (2006.01)
*A61P 43/00* (2006.01)
*C07F 9/655* (2006.01)
*C07D 417/04* (2006.01)

(52) U.S. Cl.
CPC .............. *C07D 307/46* (2013.01); *A61P 7/00* (2018.01); *A61P 43/00* (2018.01); *C07D 417/04* (2013.01); *C07F 9/65515* (2013.01)

(58) Field of Classification Search
CPC ..................................... C07D 307/46
USPC ......................................... 549/483
See application file for complete search history.

(56) References Cited

U.S. PATENT DOCUMENTS

| 7,119,208 B2 | 10/2006 | Safo et al. |
| 2012/0302768 A1 | 11/2012 | Janka et al. |
| 2015/0359787 A1 | 12/2015 | Hisamichi et al. |

FOREIGN PATENT DOCUMENTS

| WO | 2004037808 A1 | 5/2004 |
| WO | 2015002994 A2 | 1/2015 |

OTHER PUBLICATIONS

Compounds with Registry Nos. 1214846-32-8; 1214706-90-7; 1214644-90-2; 1214134-98-1; 1214077-66-3; 1214075-75-8; 1214061-50-3; all dated Mar. 24, 2010. Registry No. 1103648-98-8, dated Feb. 10, 2009.*

* cited by examiner

*Primary Examiner* — Taofiq A Solola
(74) *Attorney, Agent, or Firm* — W & C IP

(57) ABSTRACT

Prodrugs and derivatives of 5-hydoxymethyl-2-furfural (5-HMF) with protected or modified aldehyde and/or alcohol moieties are provided. The prodrugs or derivatives exhibit increased bioavailability, e.g. due to having extended half-lives in circulation. The drugs are therefore administered i) at lower doses and/or ii) less frequently than 5-HMF, while still maintaining the beneficial therapeutic effects of 5-HMF.

4 Claims, 12 Drawing Sheets

5-HMF

VZHE004  VZHE006  VZHE007  VZHE014

B. Alkyl Ether Derivatives

VZHE005  VZHE011  VZHE013  VZHE015  VZHE016

5-PMFC  5-CMFC  5-NMFC

PRODRUG AND PROTECTED FORMS OF 5-HYDROXYMETHYLFURFURANAL (5-HMF) AND ITS DERIVATIVES

CROSS-REFERENCE TO RELATED APPLICATIONS

This application claims benefit of U.S. provisional patent application 62/366,250, filed Jul. 25, 2016, and U.S. provisional patent application 62/365,563, filed Jul. 22, 2017, the complete contents of which is hereby incorporated by reference.

STATEMENT OF FEDERALLY SPONSORED RESEARCH AND DEVELOPMENT

This invention was made with government support under grant MD009124 awarded by the National Institutes of Health/National Institute on Minority Health and Health Disparities. The United States government has certain rights in the invention.

BACKGROUND OF THE INVENTION

Field of the Invention

The invention generally relates to prodrug or protected forms of 5-hydoxymethyl-2-furfural (5-HMF). In particular, the invention provides prodrug or derivative forms of the drug with protected alcohol (hydroxymethyl) and/or aldehyde functions.

Background 5-hydoxymethyl-2-furfural (5-HMF, also known as Aes-103), an aromatic aldehyde, increases oxygen affinity of sickle hemoglobin (HbS) and prevents the primary pathophysiology (hypoxia-induced sickling) associated with sickle cell disease (SCD). In addition, the drug ameliorates several of the cascading secondary adverse events, including adhesion of red blood cells (RBCs) to tissue endothelium, oxidative stress, hemolysis of RBCs, decreased vascular NO bioavailability, vaso-occlusion, impaired microvascular blood flow, increased blood pressure, and painful crises. In vitro studies show 5-HMF increases $O_2$-affinity of HbS, decreases fiber formation, reduces sickle cell mechanical fragility, and reduces RBC hemolysis. Studies in animal models show 5-HMF markedly increases survival of both sickle cell and wild-type mice under hypoxic stress by preventing sickling of RBC and/or increasing blood oxygen levels ($SpO_2$), and by attenuating hypoxia-induced cell necrosis and apoptosis. 5-HMF also provides improved microvascular function during resuscitation of hamsters from hemorrhagic shock. 5-HMF also results in hemodynamic and oxygenation benefits during hypoxia (e.g. maintenance of blood pressure and heart rate; preservation of microvascular blood flow; reduction in heart and brain hypoxia areas) in mice. 5-HMF has also progressed through Phase I/II clinical trials in healthy volunteers and adults with SCD under the NIH Therapeutics for Rare and Neglected Diseases Program, TRND (ClinicalTrials.gov; identifier NCT01597401). The study outcome indicated significant improvement in several clinical symptoms, including reduced pain, decreased lactate dehydrogenase and/or RBC hemolysis, reduction in diastolic blood pressure, and an increase in blood oxygen levels ($S_pO_2$) during hypoxia challenge.

The fundamental pathophysiology of SCD involves the polymerization of sickle Hb under low $O_2$ saturation, which is exacerbated by the fact that sickle Hb has low affinity for oxygen partly due to higher intracellular 2,3-diphosphoglycerate concentration in sickle RBCs, which paradoxically causes more $O_2$ to be prematurely released at the arteries and arterioles. 5-HMF is able to increase the oxygen affinity of sickle Hb, preventing the sickling of red blood cells. The pharmacologic effect involves both the 5-HMF aldehyde and alcohol moieties. Two molecules of 5-HMF bind to the two α-chains of hemoglobin, the aldehyde moiety forming a Schiff-base with the N-terminal Val1 nitrogen (FIG. 1). The alcohol moieties of the two bound compounds then interact through a series of intricate water-mediated interactions that tie the two α-subunits together to stabilize the relaxed state of hemoglobin (FIG. 1), thereby increasing the oxygen affinity of hemoglobin.

Although 5-HMF fits most of the criteria of a good drug candidate, because of the aldehyde and alcohol moieties, 5-HMF is subject to rapid metabolism by aldehyde dehydrogenase (ALDH) and alcohol dehydrogenase (ADH) to the carboxylate and di-aldehyde intermediates, respectively (FIG. 2). The intermediates further metabolize into three major products, including hydroxymethyl-2-furoic acid, furan-2,5-dicarboxylic acid and N-(5-hydroxymethyl-2-furoyl)-glycine. The rapid metabolism shortens the pharmacologic effect of the drug, manifesting as a very short half-life in plasma (1-1.5 hrs), both in-vitro and in-vivo. This property necessitates frequent and very high doses, consistent with the phase I/II human clinical studies that suggest an effective dose of 2-4 gm. Such a high dose is undesirable for a chronic disease, and frequent dosing in inconvenient and does not favor patient compliance.

Prodrugs of 5-HMF are known in which the aldehyde is protected with a cysteine to form a thiazolidine complex of 5-HMF. When administered orally to transgenic sickle mice, this prodrug has been shown to prolong the half-life of 5-HMF in plasma when compared to the parent 5-HMF. However, the alcohol substituent which is essential for 5-HMF potent activity is still prone to alcohol dehydrogenase metabolism.

There is a need in the art to develop derivatives or prodrugs of 5-HMF or protected 5-HMF derivatives with increased potency and/or decreased metabolism and/or longer in vivo half-lives and/or increased bioavailability.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The invention provides 5-HMF prodrugs, e.g. protected 5-HMF derivatives with improved pharmacologic properties, including but not limited to increased potency and/or lengthened half-lives, and/or improved bioavailability. In some aspects, the alcohol moiety of 5-HMF (or derivatives of 5-HMF), the aldehyde moiety or 5-HMF (or derivatives of 5-HMF), or both the alcohol and the aldehyde moieties of 5-HMF (or derivatives of 5-HMF) is/are modified with substituents e.g. protecting groups. Compared to previously known modified 5-HMF prodrugs, those described herein exhibit increased potency and/or improved bioavailability and/or extended (longer) pharmacologic effects. Therefore, lower and/or less frequent doses of the prodrugs are needed to treat e.g. sickle cell disease, compared to the typical dosages of 5-HMF. Exemplary alcohol modifying groups include: esters, carboxylic acids, natural amino acids and inorganic acids. Exemplary aldehyde modifying groups include thiazolidine moieties.

It is an object of the invention to provide prodrugs or protected forms of 5-hydoxymethyl-2-furfural (5-HMF) with a generic formula:

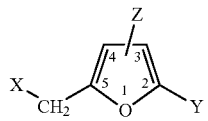

Formula I where:
X is:
  i) a carboxyl group containing moiety having Formula II

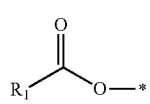

Formula II where R1 is substituted or unsubstituted alkyl, substituted or unsubstituted aryl, H, O-alkyl or halogen; and where the bond marked with * bonds directly to CH$_2$ of Formula I;
  ii) an L or D amino acid;
  iii) an inorganic acid or a salt of an inorganic acid;
  iv) an ether having Formula III

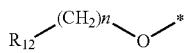

Formula III where R12=alkyl or aryl, n=0-4 and the bond marked with * bonds directly to CH$_2$ of Formula I; or
  v) a bicyclic ring system comprising a five- and a six-membered ring

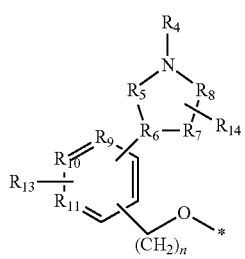

where
  the five-membered ring is saturated or unsaturated; N=nitrogen; one or more of R5, R6, R7 and R8 are independently C, N, O or S; R4 is H, alkyl, aryl, O-alkyl or O-aryl; and R14 is absent or is H, alkyl, aryl, O-alkyl or O-aryl;
  the six-membered ring is aromatic and one or more of R9, R10 and R11 are independently C or N; R13 is H, alkyl, aryl, O-alkyl or O-aryl; the bond marked with * bonds to C of CH$_2$ of Formula I via an ether linkage (—O—); and n=0-4;

Y is CHO or

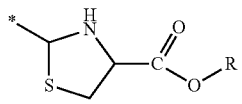

where R is H or a straight chain or branched C1-C5 alkyl; and where the bond marked with * bonds directly to carbon at position 2 of the furan ring of Formula I; and
  Z is H, OH, alkyl, aryl, O-alkyl, O-aryl or O-heteroaryl, and wherein the compound is not 5-(phenoxymethyl)-2-furan carbaldehyde (5-PMFC), 5-((2-nitrophenoxy)methyl)-2-furan carbaldehyde (5-NMFC) or 5-((4-chlorophenoxy)methyl)-2-furan carbaldehyde (5-CMFC).

In some aspects, the prodrug or protected form of 5-hydoxymethyl-2-furfural (5-HMF) of claim 1 is VZHE006:

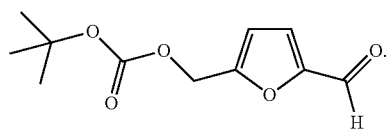

tert-butyl ((5-formylfuran-2-yl)methyl carbonate

In some aspects, the prodrug or protected form of 5-hydoxymethyl-2-furfural (5-HMF) of claim 1 is VZHE0011:

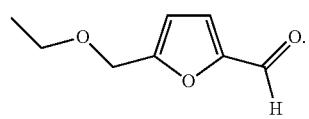

5-(ethoxymethyl)furan-2-carbaldehyde

In further aspects, the prodrug or protected form of 5-hydoxymethyl-2-furfural (5-HMF) of claim 1 is VZHE015:

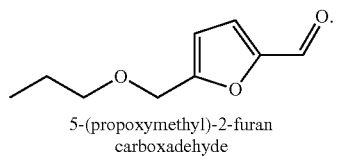

5-(propoxymethyl)-2-furan carboxadehyde

The invention also provides methods of treating or prophylactically treating sickle cell disease in a subject in need thereof, comprising administering to the subject a therapeutically effective amount of a prodrug or protected form of 5-hydoxymethyl-2-furfural (5-HMF) with a generic formula:

Formula I

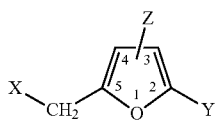

where:

X is:

i) a carboxyl group containing moiety having Formula II

Formula II

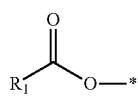

where R1 is substituted or unsubstituted alkyl, substituted or unsubstituted aryl, H, O-alkyl or halogen; and where the bond marked with * bonds directly to CH$_2$ of Formula I;

ii) an L or D amino acid;

iii) an inorganic acid or a salt of an inorganic acid;

iv) an ether having Formula III

Formula III

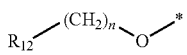

where R12=alkyl or aryl, n=0-4 and the bond marked with * bonds directly to CH, of Formula I; or v) a bicyclic ring system comprising a five- and a six-membered ring

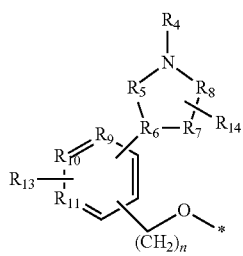

where the five-membered ring is saturated or unsaturated; N=nitrogen; one or more of R5, R6, R7 and R8 are independently C, N, O or S; R4 is H, alkyl, aryl, O-alkyl or O-aryl; and R14 is absent or is H, alkyl, aryl, O-alkyl or O-aryl;

the six-membered ring is aromatic and one or more of R9, R10 and R11 are independently C or N; R13 is H, alkyl, aryl, O-alkyl or O-aryl; the bond marked with * bonds to C of CH$_2$ of Formula I via an ether linkage (—O—);

and n=0-4;

Y is CHO or

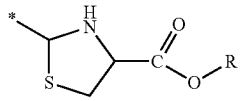

where R is H or a straight chain or branched C1-C5 alkyl; and where the bond marked with * bonds directly to carbon at position 2 of the furan ring of Formula I; and Z is H, OH, alkyl, aryl, O-alkyl, O-aryl or O-heteroaryl, and wherein the compound is not (5-Formylfuran-2-yl) methyl benzoate (VZHE007), 5-(tert-Butoxymethyl)furan-2-carbaldehyde (VZHE013), (5-Formylfuran-2-yl)methyl dimethyl phosphate (VZHE014), 5-((2-nitrophenoxy) methyl)-2-furan carbaldehyde (5-NMFC) or 5-((4-chlorophenoxy) methyl)-2-furan carbaldehyde (5-CMFC).

In some aspects, the prodrug or protected form of 5-HMF is 5-PMFC:

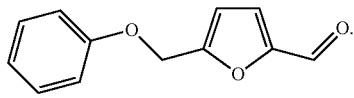

5-(phenoxymethyl)furan-2-carbaldehyde

In other aspects, the prodrug or protected form of 5-HMF is VZHE006:

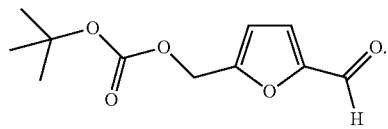

tert-butyl ((5-formylfuran-2-yl)methyl carbonate

In yet further aspects, the prodrug or protected form of 5-HMF is VZHE0011:

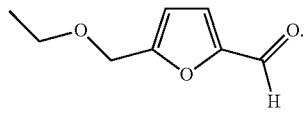

5-(ethoxymethyl)furan-2-carbaldehyde

In additional aspects, the prodrug or protected form of 5-HMF is VZHE005:

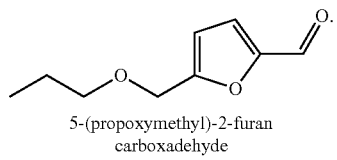

5-(propoxymethyl)-2-furan carboxadehyde

The invention further provides methods of treating or prophylactically treating hypoxia in a subject in need thereof, comprising administering to the subject a therapeutically effective amount of a prodrug or protected form of 5-hydoxymethyl-2-furfural (5-HMF) with a generic formula:

Formula I

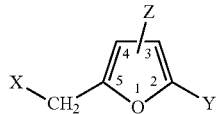

where:

X is:
i) a carboxyl group containing moiety having Formula II

Formula II

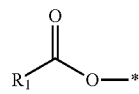

where R1 is substituted or unsubstituted alkyl, substituted or unsubstituted aryl, H, O-alkyl or halogen; and where the bond marked with * bonds directly to CH$_2$ of Formula I;
ii) an L or D amino acid;
iii) an inorganic acid or a salt of an inorganic acid;
iv) an ether having Formula III Formula III

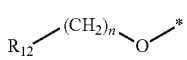

where R12=alkyl or aryl, n=0-4 and the bond marked with * bonds directly to CH, of Formula I; or
v) a bicyclic ring system comprising a five- and a six-membered ring

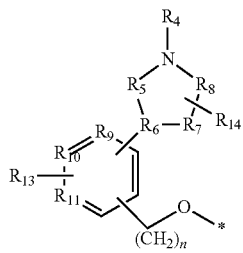

where
the five-membered ring is saturated or unsaturated; N=nitrogen; one or more of R5, R6, R7 and R8 are independently C, N, O or S; R4 is H, alkyl, aryl, O-alkyl or O-aryl; and R14 is absent or is H, alkyl, aryl, O-alkyl or O-aryl;
the six-membered ring is aromatic and one or more of R9, R10 and R11 are independently C or N; R13 is H, alkyl, aryl, O-alkyl or O-aryl; the bond marked with * bonds to C of CH$_2$ of Formula I via an ether linkage (—O—);
and n=0-4;

Y is CHO or

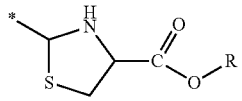

where R is H or a straight chain or branched C1-C5 alkyl; and where the bond marked with * bonds directly to carbon at position 2 of the furan ring of Formula I; and
Z is H, OH, alkyl, aryl, O-alkyl, O-aryl or O-heteroaryl.
In some aspects, the prodrug or protected form of 5-HMF is 5-PMFC:

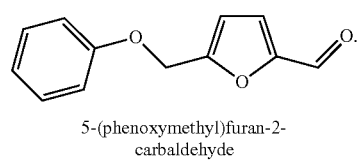 [SMILES: O=Cc1ccc(COc2ccccc2)o1]

5-(phenoxymethyl)furan-2-carbaldehyde

In other aspects, the prodrug or protected form of 5-HMF is VZHE006:

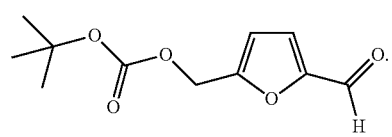

tert-butyl ((5-formylfuran-2-yl)methyl) carbonate

In further aspects, the prodrug or protected form of 5-HMF is VZHE0011:

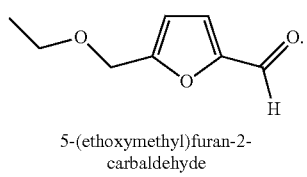

5-(ethoxymethyl)furan-2-carbaldehyde

In additional aspects, the prodrug or protected form of 5-HMF is VZHE015:

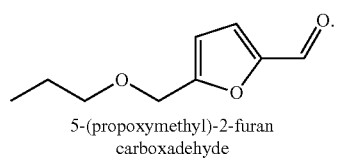

5-(propoxymethyl)-2-furan carboxadehyde

The invention also provides 5-hydroxymethyl-2-furfural (5-HMF) derivatives where at least one of the alcohol or the aldehyde moiety is substituted with a protective leaving group. In some aspects, the alcohol is substituted with the protective leaving group and the protective leaving group is a substituted or unsubstituted ether or ester selected from the group consisting of substituted or unsubstituted C1-12 alkyl ether, substituted or unsubstituted C1-12 alkyl ester, substituted or unsubstituted C1-12 aryl or alkaryl ether, substituted or unsubstituted C1-12 aryl or alkaryl ester, substituted or unsubstituted C1-12 heteroaryl or alkheteroaryl ether, and substituted or unsubstituted C1-12 heteroaryl or alkheteroaryl ester.

DETAILED DESCRIPTION

Figure 1A:
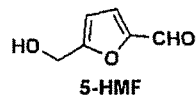
FIG. 1A-D. A, 5-hydroxymethyl-2-furfural (5-HMF); B, ester derivatives of 5-HMF; C, alkyl ether derivatives of 5-HMF; D, aryl ether derivatives of 5-HMF.
Figure 1B:
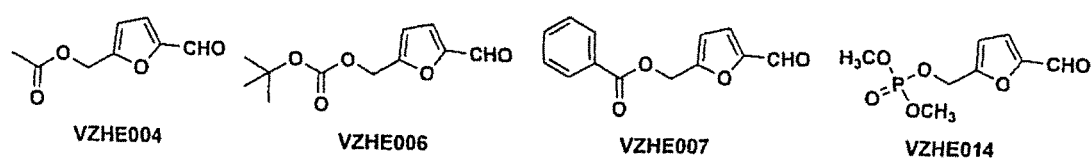
Figure 1C:
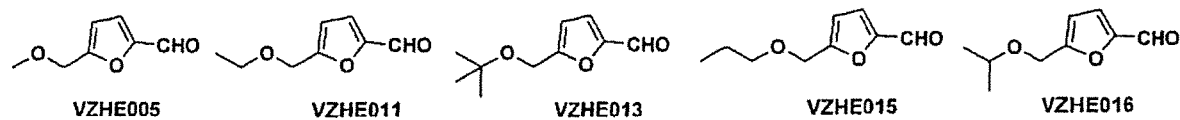
Figure 1D:
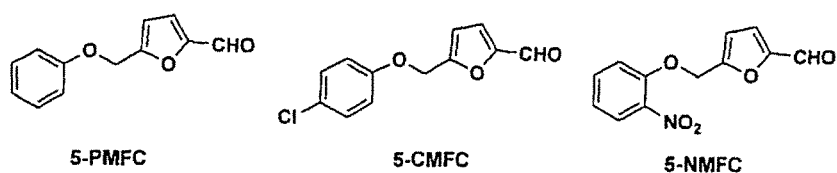

Derivatives or prodrugs of 5-HMF with protected or modified aldehyde and/or alcohol moieties are provided. In some aspects, only the aldehyde or only the alcohol moiety is protected or modified. In other aspects, both the aldehyde and the alcohol moiety are protected or modified. These prodrugs or derivatives exhibit increased potency and/or bioavailability and/or longer half-life due to improved binding affinity with Hb and/or having decreased alcohol and/or aldehyde moiety metabolism in circulation. This permits the drugs to be administered i) at lower doses and/or ii) less frequently, while still maintaining the beneficial therapeutic effects of 5-HMF, thereby minimizing side effects and/or increasing patient compliance with administration.

By "derivative" we mean a chemical compound that can be produced from another compound via one or more chemical reactions, such as replacement of $H_2OH$ etc. by an alkyl, acyl, or amino group, etc. Derivatives of a compound may also be referred to as modified forms of the compound. The synthesis of a derivative of a compound may proceed by modifying the compound directly, or by another synthetic route. Either way, the derivatized product typically has a core structure similar to that of the original compound, but one or more functional groups of the original compound have been replaced by different functional groups.

In some aspects, the compounds have the composition shown in Formula I:

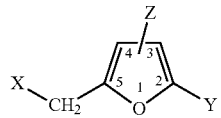

Formula I where:
1. Y is CHO (as in 5-HMF in which the aldehyde is not modified) or is

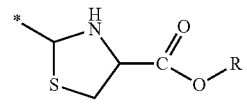

where R is H or alkyl such as a straight chain or branched C1-C12 alkyl e.g. methyl, ethyl, propyl, isopropyl, butyl (e.g. n-butyl, secondary butyl, isobutyl, tertiary butyl), pentyl (e.g. n-pentyl, tert-pentyl, neopentyl, isopentyl, sec-pentyl, 3-pentyl), etc.; and where the bond marked with a "*" bonds directly to carbon at position 2 of the furan ring of Formula I (as is 5-HMF in which the aldehyde is modified);

2. Z is H, OH, alkyl (such as a straight chain or branched C1-C12 alkyl e.g. methyl, ethyl, propyl, isopropyl, butyl (e.g. n-butyl, secondary butyl, isobutyl, tertiary butyl), pentyl (e.g. n-pentyl, tert-pentyl, neopentyl, isopentyl, sec-pentyl, 3-pentyl), etc.), aryl, O-alkyl or O-aryl. As used herein, "aryl" refers to any functional group or substituent that is or is derived from an aromatic ring, e.g. an aromatic hydrocarbon, such as phenyl, naphthyl, thienyl, indolyl, which may be substituted [e.g. with O, N, S, etc.] or unsubstituted, or halogenated, etc.). Accordingly, in some aspects, Z is phenyl or substituted phenyl; and 3. X is as described below.

In some aspects of the invention, if the alcohol moiety of 5-HMF is not modified, then Y is not a cysteinyl moiety incorporating the sulfur and nitrogen in a ring.

In additional aspects, the compound is not 5-(phenoxymethyl)-2-furan carbaldehyde (5-PMFC), 5-((2-nitrophenoxy) methyl)-2-furan carbaldehyde (5-NMFC) or 5-((4-chlorophenoxy) methyl)-2-furan carbaldehyde (5-CMFC).

Protection of the Alcohol: Exemplary Equivalents of X

I. Carboxylic Groups (e.g. Esters)

In some aspects X of Formula I is

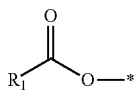

where the bond marked with "*" bonds directly to carbon of the $CH_2$ group depicted in Formula I.

In some aspects, X is an aliphatic ester, e.g. R1 is a substituted or unsubstituted alkyl, for example, a straight chain or branched C1-C12 alkyl such as methyl, ethyl, propyl, isopropyl, butyl (e.g. n-butyl, secondary butyl, isobutyl, tertiary butyl), pentyl (e.g. n-pentyl, tert-pentyl, neopentyl, isopentyl, sec-pentyl, 3-pentyl), etc. By substituted we mean containing moieties other than carbon or hydrogen e.g. halogenated, amidated, sulfonated, phosphorus-containing, nitrosylated, oxygenated, etc.

In other aspects, the X includes a substituted or unsubstituted aryl or hereroaryl. As used herein, "aryl" refers to any functional group or substituent derived from an aromatic ring, e.g. an aromatic hydrocarbon, such as phenyl, naphthyl, thienyl, indolyl, which may be substituted (e.g. with P, O, N, S, halogen, etc.) or unsubstituted. Accordingly, in some aspects, R1 is phenyl or substituted phenyl, and the compound with the carboxylic carboxyl group is:

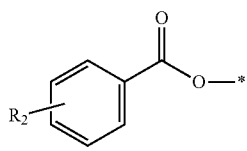

where R2 is present or absent and if present, is, for example: alkyl, e.g. a straight chain or branched C1-C12 saturated or unsaturated alkyl such as methyl, ethyl, ethane, ethyne, propyl, propylene, isopropyl, butyl (e.g. n-butyl, secondary butyl, isobutyl, tertiary butyl), pentyl (e.g. n-pentyl, tert-pentyl, neopentyl, isopentyl, sec-pentyl, 3-pentyl), etc.; halide substituted alkyl (e.g. $CH_7Cl$); O-alkyl; O-aryl; an electron withdrawing group (e.g. $NO_2$, a halide, an ester, a sulfone, quaternary ammonium, SH, OH, etc.), or other suitable group; and where the bond marked with "*" bonds directly to the carbon of the $CH_2$ group depicted in Formula 1.

In some aspects, the R1 is a substituted or unsubstituted heteroaryl (e.g. pyridine, pyrimidine, etc.). Substitutions, if present, are the same as set forth above. Heteroaryls are a subset of aryls in the practice of the invention.

In other aspects, R1 is O-alkyl (where "alkyl" is as described above), O-aryl (where "aryl" is as described above), or halogen (e.g. Cl, Br, or I).

In yet further aspects, R1 is an unsaturated hydrocarbon having from about 3 to about 15 carbons and comprising one or more double or triple bonds, e.g. an alkene, an alkyne, a diene, etc.

II. Equivalents of X: Amino Acids

In some aspects, X is an L or D amino acid,

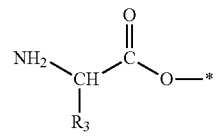

where the bond marked with "*" bonds directly to carbon of the $CH_2$ group depicted in Formula I, and R3 is a hydrophobic, acidic, basic or polar amino acid side chain such as:

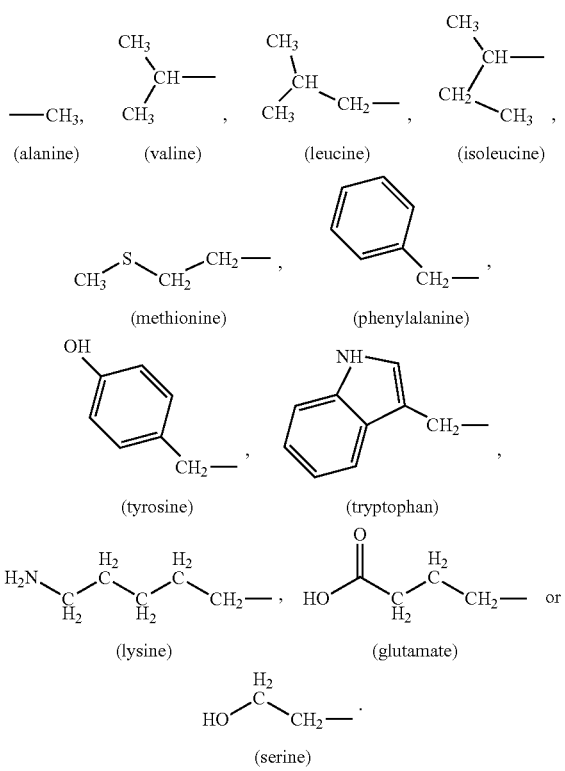

III. Equivalents of X: Inorganic Acids

In some aspects, X is an inorganic acid or a salt of an inorganic acid such as

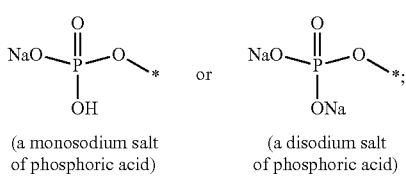

and where the bond marked with "*" bonds directly to carbon of the $CH_2$ group depicted in Formula I.

IV. Equivalents of X: 0-Linked Alkyls, Aryls, and Bicyclic Ring Systems (Ethers)

In some aspects, X is an O-aryl or O-alkyl

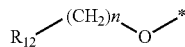

where the bond marked with "*" bonds directly to carbon of the CH$_2$ group of Formula I and where n=0-4. In some embodiments, R12 is a straight chain or branched C1-C5 saturated or unsaturated alkyl e.g. methyl, ethyl, ethane, ethyne, propyl, propylene, isopropyl, butyl (e.g. n-butyl, secondary butyl, isobutyl, tertiary butyl), pentyl (e.g. n-pentyl, tert-pentyl, neopentyl, isopentyl, sec-pentyl, 3-pentyl), halide substituted alkyl (e.g. CH$_2$Cl), etc. In other aspects, R12 is aryl, i.e. a functional group or substituent derived from an aromatic ring, e.g. an aromatic hydrocarbon, such as phenyl, naphthyl, thienyl, indolyl, which may be substituted (e.g. with O, N, S, etc.) or unsubstituted, or halogenated, etc.

In some aspects, the compound is not 5-PMFC, 5CMFC or 5-NMFC.

In some aspects, X is a bicyclic ring system comprising a substituted or unsubstituted five-membered ring and a substituted or unsubstituted six-membered ring

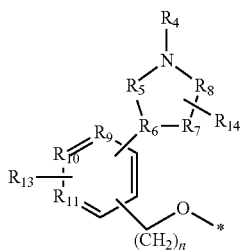

where the five-membered ring is saturated (contains no double bonds) or unsaturated (contains one or more double bonds, C=C, e.g. between R5 and R6, and/or between R8 and R7, and/or between R6 and R7, as chemically possible); N=nitrogen; one or more of R5, R6, R7 and R8 are independently C, N, O or S; R4 is H, alkyl (as described elsewhere herein), aryl (as described elsewhere herein), O-alkyl or O-aryl; R14 is absent or is alkyl (as described elsewhere herein), aryl (as described elsewhere herein), O-alkyl or O-aryl, and n=0-4;
and where the six-membered ring is aromatic (as shown) and one or more of R9, R10 and R11 are independently C or N; and R13 is H, alkyl, aryl, O-alkyl or O-aryl (see above for detailed description of aryl and alkyl as used here) and where the bond marked with * bonds to C of CH$_2$ shown in Formula I via an ether linkage (—O—).

Examples of suitable bicyclic ring systems that may be used include but are not limited to: 3-(chloromethyl)-2-(1-isopropyl-1H-pyrazole-5-yl)pyridine, 3-(bromomethyl)-2-(1-isopropyl-1H-pyrazole-5-yl)pyridine, 5-(chloromethyl)-4-(1-isopropyl-1H-pyrazol-5-yl)pyrimidine, etc.

In preferred embodiments, the alcohol of 5HMF is protected, with X being a substituted or unsubstituted ester or ether (see sections I and IV above). In particular, X is a substituted or unsubstituted ether or ester selected from the group consisting of substituted or unsubstituted C1-12 alkyl ether, substituted or unsubstituted C1-12 alkyl ester, substituted or unsubstituted C1-12 aryl or alkaryl ether, substituted or unsubstituted C1-12 aryl or alkaryl ester, substituted or unsubstituted C1-12 heteroaryl or alkheteroaryl ether, and substituted or unsubstituted C1-12 heteroaryl or alkheteroaryl ester.

Exemplary Benefits of the Prodrugs

The 5-HMF prodrugs or protected derivatives described herein exhibit improved pharmacologic activity, i.e. more potency and/or increased (lengthened, longer-lasting, etc.) half-lives, and/or improved bioavailability under physiological conditions (e.g. in circulation, in plasma, etc.) compared to 5-HMF and previous forms of 5-HMF. In some aspects, compared to 5-HMF, the prodrugs or derivatives exhibit half-lives of greater than about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5 or 12.0 hours, or even longer, e.g. about 12 to 36 hours, i.e. about 12, 14, 16, 18, 20, 22, 24, 26, 28, 30, 32, 34 or 36 hours. In some aspects, compared to 5-HMF, the prodrugs or derivatives exhibit 1, 2, 3, 4, 5, 6, 7, 8, 9, or 10-fold greater potency. Thus, in some aspects, the compositions comprising the prodrugs or derivatives are administered less frequently and yet the same or an increased level of beneficial effects is experienced by subjects receiving the prodrugs or protected derivatives.

In addition, in some aspects, more than one type of prodrug or derivative is administered to the subject, e.g. one "dose" may include i) a prodrug or derivative (or even 5-HMF) that is metabolized and provides relief of symptoms soon after administration (e.g. within and for about 1-2 hours) and ii) at least one additional prodrug or derivative (in the same composition, or administered in a different composition but at approximately the same time) that is metabolized (activated) more slowly and does not exert its effects (or its peak effects) until about 2-4 hours (or more) later. Additional prodrug or derivative forms with a "laddered" time of maximum activation/activity may be included in a single "dose" of medicament, e.g. about 1-4, 4-8, 8-12 hours; or from about 1-6 and 6-12 hours; or from about 1-12 and 12-24 hours, etc.

Exemplary Methods of Treatment Using the Prodrugs or Derivatives

The prodrugs or derivatives described herein are used to treat or prophylactically treat any disease or condition that is amenable to treatment with 5-HMF. In some aspects, the prodrug that is used is not 5-CMFC, VZHE007, VZHE0013 or VZHE0014. As used herein, "prophylactically treat" ("prophylactic treatment", "prophylactically treating" etc.) and "prevent" ("prevention", "preventing" etc.) refer to warding off or averting the occurrence of at least one symptom of a disease or unwanted condition (such as at least one symptom of SCD), by prophylactic administration of a composition comprising at least one prodrug or derivative as described herein, to a subject in need thereof. Generally, "prophylactic" or "prophylaxis" relates to a reduction in the likelihood of the patient developing a disorder or a symptom of a disorder. Typically, the subject is considered by one of skill in the art to be at risk of or susceptible to developing at least one symptom of the disease or unwanted condition, or is considered to be likely to develop at least one symptom of the disease/condition in the absence of medical intervention. In some aspects, for "prevention" or "prophylactic treatment", administration occurs before the subject has, or is known or confirmed to have, symptoms of the disease (condition, disorder, syndrome, etc.; unless otherwise indicated, these terms are used interchangeably herein). In other words, symptoms may not yet be overt or observable, or may be very "early stage" symptoms. The subject may be considered at risk due to a variety of factors, including but not limited to: genetic predisposition; evidence of "early" symptoms; etc. In such aspects, treatment of the subject may prevent the noxious or harmful effects or outcomes (results) of full blown disease. "Prevention" or "prophylactic treatment" of a disease or condition may involve completely preventing the occurrence of detectable symptoms, or, alternatively, may involve lessening or attenuating the degree, severity or duration of at least one symptom of the disease that would occur in the absence of the medical interventions provided herein. "Treat" (treatment, treating, etc.) as used herein refers to administering at least one composition comprising a prodrug or derivative as described herein, to a subject that already exhibits at least one symptom of a disease such as SCD. In other words, at least one parameter that is known to be associated with the disease has been measured, detected or observed in the subject. For example, the symptom may be the primary pathophysiology of hypoxia-induced RBC sickling associated with sickle cell disease. In addition, the drug ameliorates several of the cascading secondary adverse events, including adhesion of RBCs to tissue endothelium, oxidative stress, hemolysis of RBCs, decreased vascular NO bioavailability, vaso-occlusion, impaired microvascular blood flow, increased blood pressure, and painful crises. In vitro studies show 5-HMF increases $O_2$-affinity of HbS, decreases fiber formation, reduces sickle cell mechanical fragility, and reduces RBC hemolysis. Studies in animal models show 5-HMF markedly increases survival of both sickle cell and wild-type mice under hypoxic stress by preventing sickling of RBC and/or increasing blood oxygen levels ($SpO_2$), and by attenuating hypoxia-induced cell necrosis and apoptosis. 5-HMF also provides improved microvascular function during resuscitation of hamsters from hemorrhagic shock. 5-HMF also results in hemodynamic and oxygenation benefits during hypoxia (e.g. maintenance of blood pressure and heart rate; preservation of microvascular blood flow; reduction in heart and brain hypoxia areas) in mice. 5-NMF has also progressed through Phase I/II clinical trials in healthy volunteers and adults with sickle cell disease (SCD) under the NIH Therapeutics for Rare and Neglected Diseases Program, TRND (ClinicalTrials.gov; identifier NCT01597401). The study outcome indicated significant improvement in several clinical symptoms, including reduced pain, decreased lactate dehydrogenase and/or RBC hemolysis, reduction in diastolic blood pressure, and increase in blood oxygen levels ($S_pO_2$) during hypoxia challenge.

"Treatment" of a disease involves the lessening or attenuation, or in some instances, the complete eradication, of at least one symptom of the disease that was present prior to or at the time of administration of the composition.

Exemplary Compositions Comprising the Prodrugs and/or Derivatives and Methods of Administering the Prodrug or Derivative Compositions Provided herein are compositions comprising at least one 5-HMF as described herein, and methods of administering the same to treat e.g. SCD, hypoxia, etc. Implementation of the methods generally involves identifying patients suffering from or at risk of developing a disease or condition described herein (for example SCD or hypoxia), and administering a composition as described herein by an appropriate route. The exact dosage to be administered may vary depending on the age, gender, weight and overall health status of the individual patient, or on other treatments being received by the patient, as well as the extent or progression of the disease condition being treated and the precise etiology of the disease. However, in general for administration to mammals (e.g. humans), sufficient composition is administered to achieve prodrug or derivative dosages in the range of from about 0.1 to about 60 mg or more per kg of body weight per 24 hr., and preferably about 0.1 to about 30 mg of prodrug or derivative per kg of body weight per 24 hr., and more preferably about 0.1 to about 10 mg of prodrug or derivative per kg of body weight per 24 hr. are effective. Accordingly, daily doses (in terms of prodrug or derivative) generally range from about 6 milligram to about 3600 milligrams per person per day. In some aspects, the dose is from about 10 milligrams to about 2000 milligrams per person per day, or about 100 milligrams to about 1000 milligrams per person per day. The dose will vary with the route of administration, the bioavailability, and the particular formulation that is administered, as well as according to the nature of the malady that is being prevented or treated.

The compositions are generally administered in a pharmaceutically acceptable formulation which includes suitable excipients, elixirs, binders, and the like (generally referred to as "pharmaceutically and physiologically acceptable carriers"), which are pharmaceutically acceptable and compatible with the active ingredients. The prodrugs or derivatives may be present in the formulation as pharmaceutically acceptable salts (e.g. alkali metal salts such as sodium, potassium, calcium or lithium salts, ammonium, etc.) or as other complexes. It should be understood that the pharmaceutically acceptable formulations include solid, semi-solid, and liquid materials conventionally utilized to prepare solid, semi-solid and liquid dosage forms such as tablets, capsules, liquids, aerosolized dosage forms, and various injectable forms (e.g. forms for intravenous administration), etc. Suitable pharmaceutical carriers include but are not limited to inert solid diluents or fillers, sterile aqueous solutions and various organic solvents. Examples of solid carriers (diluents, excipients) include lactose, starch, conventional disintegrating agents, coatings, lactose, terra alba, sucrose, talc, gelatin, agar, pectin, acacia, magnesium stearate, stearic acid and lower alkyl ethers of cellulose. Examples of liquid carriers include but are not limited to various aqueous or oil based vehicles, saline, dextrose, glycerol, ethanol, isopropanol, phosphate buffer, syrup, peanut oil, olive oil, phospholipids, fatty acids, fatty acid amines, polyoxyethylene, isopropyl myristate, ethyl cocoate, octyl cocoate, polyoxyethylenated hydrogenated castor oil, paraffin, liquid paraffin, propylene glycol, celluloses, parabens, stearyl alcohol, polyethylene glycol, isopropyl myristate, phenoxyethanol, and the like, or combinations thereof. Water may be used as the carrier for the preparation of compositions which may also include conventional buffers and agents to render the composition isotonic. Oral dosage forms may include various thickeners, flavorings, diluents, emulsifiers, dispersing aids, binders, coatings and the like. The composition of the present disclosure may contain any such additional ingredients so as to provide the composition in a form suitable for the intended route of administration. In addition, the composition may contain minor amounts of auxiliary substances such as wetting or emulsifying agents, pH buffering agents, and the like. Similarly, the carrier or diluent may include any sustained release material known in the art, such as glycerol monostearate or glycerol distearate, alone or mixed with wax. Other potential additives and other materials (preferably those which are generally regarded as safe [GRAS]) include: colorants; flavorings; surfactants (TWEEN®, oleic acid, etc.); and solvents, stabilizers, binders or encapsulants (lactose, liposomes, etc.). Preservatives such as methyl paraben or benzalkium chloride may also be used. Depending on the formulation, it is expected that the active components (e.g. at least one prodrug or derivative) will be present at about 1% to about 99% of the composition and the vehicular "carrier" will constitute about 1% to about 99% of the composition. The pharmaceutical compositions of the present disclosure may include any suitable pharmaceutically acceptable additives or adjuncts to the extent that they do not hinder or interfere with the therapeutic effect(s) of the composition. Still other suitable formulations for use in the present disclosure can be found, for example in Remington's Pharmaceutical Sciences 22nd edition, Allen, Loyd V., Jr editor (September 2012); and Akers, Michael J. Sterile Drug Products: Formulation, Packaging, Manufacturing and Quality; publisher Informa Healthcare (2010).

The compositions (preparations) of the present disclosure are formulated for administration by any of the many suitable means which are known to those of skill in the art, including but not limited to: orally, by injection, rectally, by inhalation, intravaginally, intranasally, topically, as eye drops, via sprays, transdermally, sublingually, by rectal and buccal delivery, by inhalation of an aerosol, by microneedle delivery, etc. In some aspects, the mode of administration is oral, by injection or intravenously.

The administration of the compound of the present disclosure may be intermittent, or at a gradual or continuous, constant or controlled rate (e.g. in a sustained release formulation which further extends the time of bioavailability, or IV). In addition, the time of day and the number of times per day that the pharmaceutical formulation is administered may vary and are best determined by a skilled practitioner such as a physician.

Administration of the compound by any means may be carried out as a single mode of therapy, or in conjunction with other therapies and treatment modalities, e.g. antibiotics, pain medication, hydroxyurea, vaccinations, blood transfusions, provision of supplemental oxygen, gene therapy, nitric oxide, drugs to boost fetal hemoglobin production, statins, etc. In addition, if hypoxia due to heart conditions is the indication, then additional treatments for heart disease may be provided, including surgery, as may various neutraceuticals, diet regimens, exercise, etc. "In conjunction with" refers to both administration of a separate preparation of the one or more additional agents, and also to inclusion of the one or more additional agents in a composition of the present disclosure.

The subject to whom the composition is administered is generally a mammal, frequently a human, but this is not always the case. Veterinary applications of this technology are also contemplated, e.g. for companion pets (cats, dogs, etc.), or for livestock and farm animals, for horses, and even for "wild" animals that have special value or that are under the care of a veterinarian, e.g. animals in preserves or zoos, injured animals that are being rehabilitated, etc.

Diseases and Conditions that are Treated Using the 5-HMF Prodrugs or Derivatives In some aspects, the disease or condition that is prevented or treated as described herein is sickle cell disease and pathophysiologies associated with SCD, such as hypoxia-induced RBC sickling. In addition, the prodrugs or derivatives ameliorate cascading secondary adverse events, including adhesion of RBCs to tissue endothelium, oxidative stress, hemolysis of RBCs, decreased vascular NO bioavailability, vaso-occlusion, impaired microvascular blood flow, increased blood pressure, and painful crises. In addition, the prodrugs or derivatives increase $O_2$-affinity of HbS, decrease fiber formation, reduce sickle cell mechanical fragility, increase blood oxygen levels ($SpO_2$) and reduce RBC hemolysis.

In other aspects, the prodrugs or derivatives are used to treat or prevent symptoms of hypoxia that is or is not related to SCD. As used herein hypoxia (also known as hypoxiation) is a condition in which the body or a region of the body is deprived of adequate oxygen supply at the tissue level. Hypoxia is classified as either generalized, affecting the whole body, or local, affecting a region of the body. There are four types of hypoxia: (1) the hypoxemic type, in which the oxygen pressure in the blood going to the tissues is too low to saturate the hemoglobin; (2) the anemic type, in which the amount of functional hemoglobin is too small, and hence the capacity of the blood to carry oxygen is too low; (3) the stagnant type, in which the blood is or may be normal but the flow of blood to the tissues is reduced or unevenly distributed; and (4) the histotoxic type, in which the tissue cells are poisoned and are therefore unable to make proper use of oxygen. Diseases of the blood, the heart and circulation, and the lungs may all produce some form of hypoxia.

Generalized hypoxia occurs, for example, in healthy people when they ascend to high altitude, where it causes altitude sickness leading to potentially fatal complications such as high altitude pulmonary edema (HAPE) and high altitude cerebral edema (HACE). Hypoxia also occurs in healthy individuals when breathing mixtures of gases with a low oxygen content, e.g. while diving underwater and especially when using closed-circuit rebreather systems that control the amount of oxygen in the supplied air. Hypoxia also occurs as a consequence of preterm birth in the neonate due to immature lung development. Hypoxia resulting from ischemia (insufficient blood flow to a tissue or organ), is referred to as 'ischemic hypoxia' and is caused by e.g. an embolic event, a heart attack that decreases overall blood flow, or trauma to a tissue that results in damage, or may be purposefully induced in some medical procedures, e.g. implantation of a stent, application of a tourniquet, etc. Diseases such as peripheral vascular disease can cause local hypoxia. Other causes include alterations in respiratory drive, such as in respiratory alkalosis, physiological or pathological shunting of blood, diseases interfering in lung function resulting in a ventilation-perfusion mismatch, such as a pulmonary embolus, or alterations in the partial pressure of oxygen in the environment or lung alveoli. When hemoglobin is deficient, anemia can result and can cause 'anaemic hypoxia' if tissue perfusion is decreased. Carbon monoxide poisoning can cause hypoxia, either acutely, as with smoke intoxication, or over a period of time, as with cigarette smoking or exposure to smog. Certain odorless asphyxiant gases (e.g. nitrogen, methane, etc.) induce hypoxia as does cyanide poisoning and the formation of methemoglobin e.g. by ingesting sodium nitrite or certain other drugs and chemicals. The prodrugs or derivatives described herein are used to prevent or treat symptoms of one or more of any of these hypoxia-related conditions. In addition, the prodrugs or derivatives attenuate hypoxia-induced cell necrosis and apoptosis, improve microvascular function during resuscitation from hemorrhagic shock, result in hemodynamic and oxygenation benefits during hypoxia (e.g. maintenance of blood pressure and heart rate; preservation of microvascular blood flow; reduction in heart and brain hypoxia areas, etc.), and provide improvement in several clinical symptoms, including reduced pain, decreased lactate dehydrogenase and/or RBC hemolysis, reduction in diastolic blood pressure, and an increase in blood oxygen levels ($S_pO_2$) during hypoxia challenge.

Synthesis of the Prodrugs or Derivatives

Also provided herein are schematic methods of synthesizing (manufacturing) several classes of the 5-HMF prodrugs or derivatives. The details of the synthesis methods used to make the prodrugs or derivatives described herein are provided in the Examples below.

Shown below are representative, exemplary general schemes for synthesizing several classes of the compounds:

Schemes 1-7: Synthesis of selected alcohol protection compounds

Scheme 1

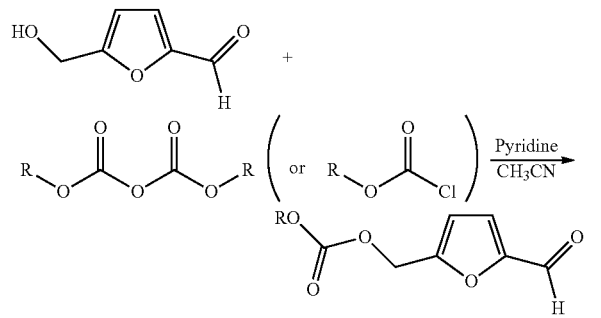

R is alkyl, aryl or see text for exhaustive description

Example

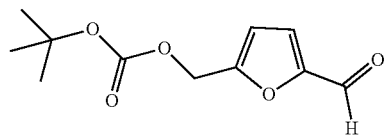 [SMILES: CC(C)(C)OC(=O)OCc1ccc(C=O)o1]

Scheme 2

R is alkyl, aryl or see text for exhaustive description

Examples

-continued

Scheme 3

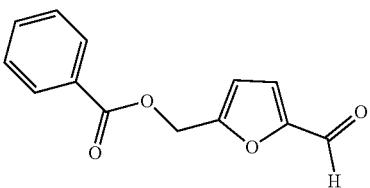

R is alkyl, aryl, metal or see text for exhaustive description.

Example

Scheme 4

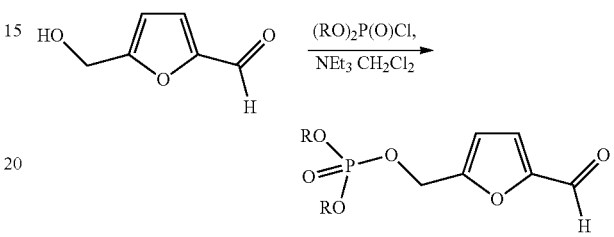

Scheme 5

R = alkyl

-continued
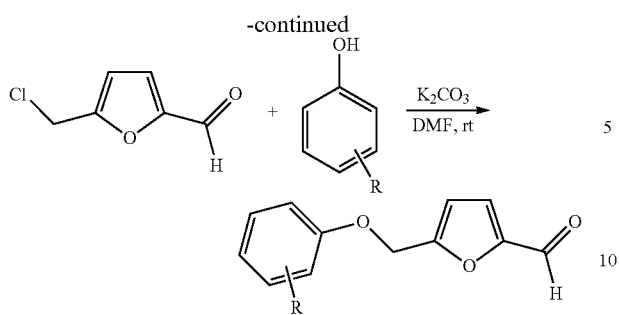
R is alkyl, aryl, bicyclic ring or see text for exhaustive description.
Scheme 6
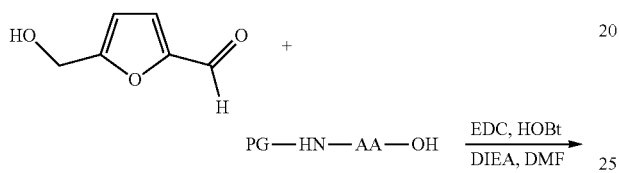
PG is protecting groups, e.g. Boc, Fmoc, cBz etc
AA is amino acid
R1, R2 or R3 are independently C or N, and R4, R6 or R7 are independently C, N, O or S, and R5 is alkyl or see text for exhaustive description
Example
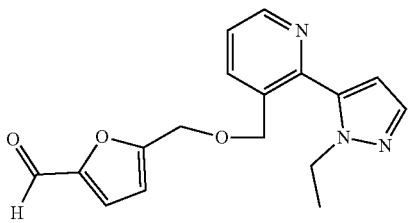 [SMILES: CCn1nccc1-c1ncccc1COCc1ccc(C=O)o1]
Scheme 8
Synthesis of selected double protection compounds
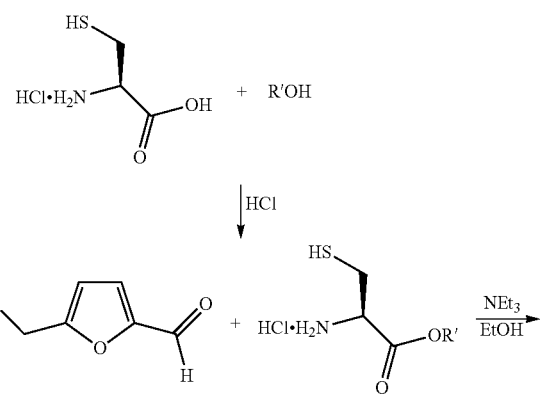
Scheme 7
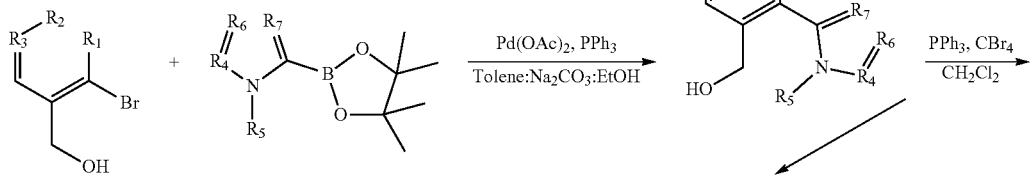
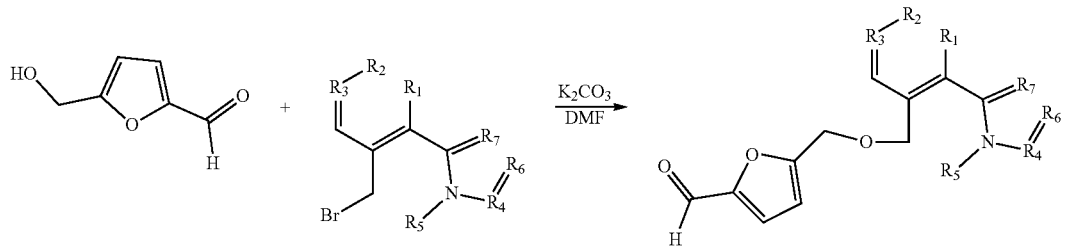

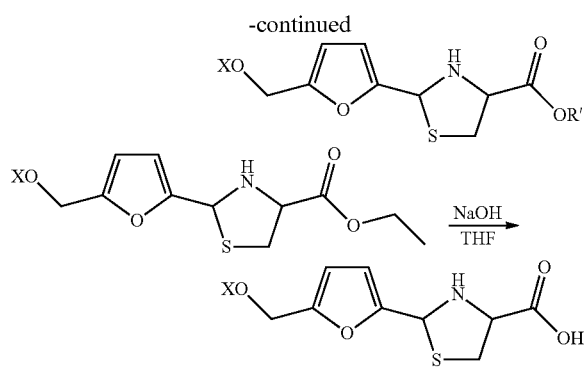

R is alkyl, aryl, etc or see text for exhaustive description
X=aryl, carboxylic acid, alkyl, etc or see text for exhaustive description Example

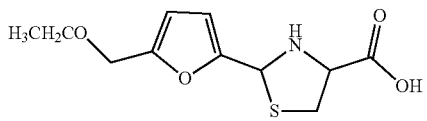

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to e.g. a tenth of the unit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Several derivatives have been synthesized and tested, including: the esters: VZHE006, VZHE007, VZHE014; the alkyl ethers: VZHE011, VZHE013, VZHE015, VZHE016; and the aryl ethers: 5-PMFC, 5-CMFC and 5-NMFC (FIG. 1). The synthetic pathways adopted for the preparation of nine of the above compounds (VZHE analogs) are outlined in Schemes 1-4, and detailed syntheses are described in the experimental section. The aryl ether compounds (5-PMFC, 5-CMFC, and 5-NMFC) were available and purchased from Sigma. All compounds were tested for their effect on Hb oxygen affinity, Hb modification, and sickle RBC morphology, and the X-ray crystallographic binding interactions of VZHE004 with Hb determined.

Scheme 1

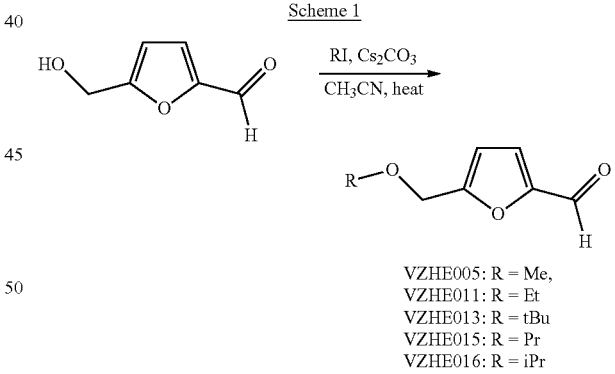

VZHE005: R = Me,
VZHE011: R = Et
VZHE013: R = tBu
VZHE015: R = Pr
VZHE016: R = iPr

Scheme 2

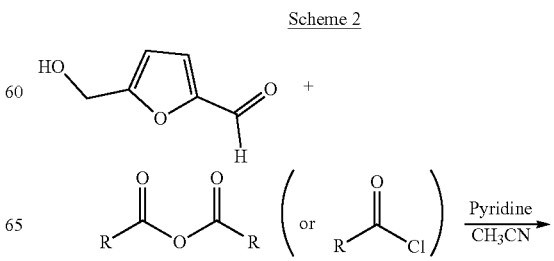

-continued

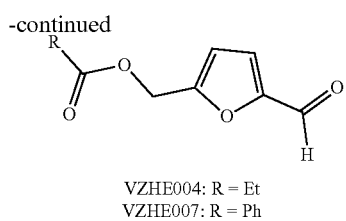

VZHE004: R = Et
VZHE007: R = Ph

Scheme 3

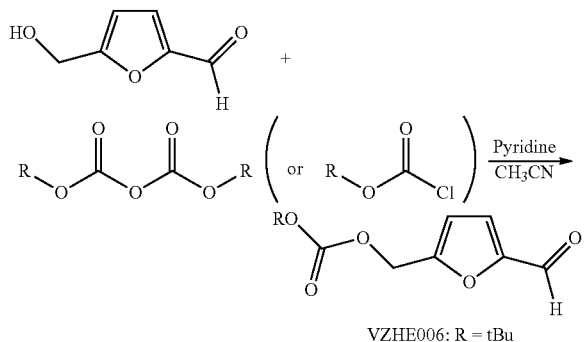

VZHE006: R = tBu

Scheme 4

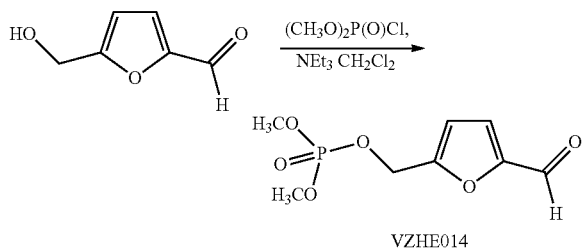

VZHE014

Experimental Procedures

Materials and General Procedure

Normal whole blood was obtained from healthy adult donors at the Virginia Commonwealth University after informed consent, in accordance with regulations of the IRB for Protection of Human Subjects. Hb was purified from discarded normal blood samples using standard procedures. Leftover blood samples from patients with homozygous SS blood were obtained and utilized, based on an approved IRB protocol at the Children's Hospital of Philadelphia, with informed consent.

All other reagents used in the syntheses and functional assays were purchased from Sigma-Aldrich (St. Louis, Mo.) and ThermoFisher Scientific (Waltham, Mass.) and utilized without additional purification. 5-(phenoxymethyl)-2-furan carbaldehyde (5-PMFC), 5-((2-nitrophenoxy)methyl)-2-furan carbaldehyde (5-NMFC), and 5-((4-chlorophenoxy) methyl)-2-furan carbaldehyde (5-CMFC) were obtained from Aldrich and used without further purification. However, synthesis methods for these three compounds are described below. Melting points were determined on a Fisher-Scientific melting point apparatus, and were uncorrected. $^1$H-NMR and $^{13}$C-NMR spectra were obtained on a Brucker 400 MHz spectrometer and tetramethylsilane (TMS) was used as an internal standard. Peak positions are given in parts per million ($\delta$). Column chromatography was performed on silica gel (grade 60 mesh; Bodman Industries, Aston, Pa.). Routine thin-layer chromatography (TLC) was performed on silica gel GHIF plates (250 μm, 2.5×10 cm; Analtech Inc., Newark, Del.). MS spectra were obtained from a Perkin Elmer Flexar UHLPC with AxION® 2 Time of Flight (TOF) Mass Spectrometer, and the molecular weight of the compounds was within 0.05% of calculated values. Infrared spectra were obtained on a Thermo Nicolet iS10 FT-IR. Purity of the compounds was determined by HPLC using a Varian Microsorb™ 100-5 C18 column (250×4.6 mm), and a Prostar 325 UV-Vis (254 nm) as the detector. UPLC-MS data were obtained using Waters® Acquity H-Class UPLC coupled to a tandem quadrupole electrospray ionisation mass spectrometry (ESI-MS detector and a Photodiode Array Detector.

I. Protection of the Hydroxymethyl Group of 5-HMF with Esters (5-formylfuran-2-yl)methyl acetate (VZHE004)

5-HMF (63 mg, 0.5 mmol) and acetic anhydride (102 mg, 1 mmol) were dissolved in 2 mL of ACN, and the mixture was cooled to 0° C. Pyridine (79 mg, 1 mmol) was added slowly. The resultant reaction mixture was stirred at 0° C. for 30 min and then at rt for 15 h. The reaction mixture was diluted with EtOAc (15 mL), and then washed with 0.1 N HCl (5 mL×3), 10% NaHCO$_3$ (5 mL×2), and brine (5 mL). The organic layer was then dried with Na$_2$SO$_4$. After filtration and concentration, the resultant crude oil was purified with column, and eluted with the solvent system of EtOAc: hexanes=1:4 to give 52 mg of the product as a colorless oil, and the yield was 62%. $^1$H-NMR (CDCl$_3$): $\delta$ 9.64 (s, 1H), 7.20 (d, J=3.52 Hz, 1H), 6.58 (d, J=3.56 Hz, 1H), 5.12 (s, 2H), 2.11 (s, 3H). $^{13}$C-NMR (CDCl$_3$): $\delta$ 177.92, 170.41, 155.61, 153.08, 121.58, 112.66, 57.96, 20.80.

tert-Butyl ((5-formylfuran-2-yl)methyl) carbonate (VZHE006)

5-HMF (1.26 g, 10 mmol) and di-tert-butyl dicarbonate (Boc$_2$O) (4.36 g, 20 mmol) were dissolved in 40 mL of CH$_2$Cl$_2$, and the mixture was cooled to 0° C. Pyridine (1.58 g, 20 mmol) was added slowly. The resultant reaction mixture was stirred at 0° C. for 30 min and then at rt for 15 h. The reaction mixture was diluted with EtOAc (150 mL), and then washed with 0.1 N HCl (50 mL×3), 10% NaHCO$_3$ (50 mL×2), and brine (50 mL). The organic layer was then dried with Na$_2$SO$_4$. After filtration and concentration, the resultant crude oil was purified with column, and eluted with the solvent system of EtOAc:hexanes=1:6 to give 1.8 g of the product as a colorless oil, and the yield was 80%. IR, 2984.4, 1740.9, 1678.7, 1524.8, 1369.4, 1272.5, 1250.6, 1153.2, 1085.9, 854.1, 812.1, 791.8, 766.4. 753.5. $^1$H-NMR (CDCl$_3$): $\delta$ 9.65 (s, 1H), 7.20 (d, J=3.56 Hz, 1H), 6.61 (d, J=3.52 Hz, 1H), 5.11 (s, 2H), 1.50 (s, 9H). $^{13}$C-NMR (CDCl$_3$): $\delta$ 177.89, 155.15, 153.00, 152.88, 121.14, 112.57, 83.21, 60.19, 27.73.

(5-Formylfuran-2-yl)methyl Benzoate (VZHE007)

5-HMF (122 mg, 1 mmol) and benzoyl chloride (280 mg, 2 mmol) were dissolved in 4 mL of CH$_2$Cl$_2$. The mixture was cooled to 0° C. and triethyl amine (202 g, 2 mmol) was added slowly. The resultant reaction mixture was stirred at 0° C. for 30 min and then at rt for 15 h. After filtration, the reaction mixture was diluted with EtOAc (15 mL), and then washed with 0.1 N HCl (5 mL×3), 10% NaHCO$_3$ (5 mL×2), and brine (5 mL). The organic layer was then dried with $Na_2SO_4$. After filtration and concentration, the resultant crude oil was purified with column, and eluted with the solvent system of EtOAc:hexanes=1:8 to give 200 mg of the product as white solid, and the yield was 90%. M.P.: 50-51° C. IR: 3122.5, 2852.2, 1708.7, 1671.1, 1253.2, 812.6, 773.2, 701.4. $^1$H-NMR (CDCl$_3$): δ 9.66 (s, 1H), 8.05 (m, 2H), 7.58 (t, J=7.54 Hz, 1H), 7.45 (t, J=7.76 Hz, 2H), 7.23 (d, J=3.52 Hz, 1H), 6.68 (d, J=3.52 Hz, 1H), 5.42 (s, 2H). $^{13}$C-NMR (CDCl$_3$): δ 177.83, 165.94, 155.56, 152.97, 133.44, 129.85, 129.35, 128.49, 121.56, 112.73, 58.25.

(5-Formylfuran-2-yl)methyl Dimethyl Phosphate (VZHE014)

5-HMF (183 mg, 1.5 mmol) and dimethyl chlorophosphate (217 mg, mmol) were dissolved in 4 mL of $CH_2Cl_2$. The mixture was cooled to 0° C., and pyridine (130 mg, 1.65 mmol) was added slowly. The resultant reaction mixture was stirred at 0° C. for 30 min and then at rt for 15 h. After filtration, the reaction mixture was diluted with EtOAc (15 mL), and then washed with 0.1 N HCl (5 mL×3), 10% NaHCO$_3$ (5 mL×2), and brine (5 mL). The organic layer was then dried with $Na_2SO_4$. After filtration and concentration, the resultant crude oil was purified with column, and eluted with the solvent system of EtOAc:hexanes=1:2 and then EtOAc to give 180 mg of the product as a colorless oil, and the yield was 51%. IR: 2959.34, 1675.9, 1525.5, 1267.5, 1008.8, 845.0, 754.0. $^1$H-NMR (CDCl$_3$): δ 9.66 (s, 1H), 7.23 (d, J=3.52 Hz, 1H), 6.67 (d, J=3.56 Hz, 1H), 5.10 (d, J=9.04 Hz, 2H), 3.78 (d, J=11.2 Hz, 6H). $^{13}$C-NMR (CDCl$_3$): δ 177.95, 155.17 (d, $^3J_{P-C}$=7.15 Hz), 153.17, 121.56, 112.70, 60.89 (d, $^2J_{P-C}$=4.83 Hz), 54.68 (d, $^2J_{P-C}$=5.96 Hz). $^{31}$P-NMR (CDCl$_3$): δ, 1.07. MS: [M+Na]$^+$ 257.0219

II. Protection of the Hydroxymethyl Group of 5-HMF with Ethers 5-(Methoxymethyl)-2-furan Carboxadehyde (VZHE005)

5-HMF (126 mg, 1.0 mmol) was dissolved in acetonitrile (5 mL), and MeI (3.0 mmol) was added and followed by Cs$_2$CO$_3$ (1.5 mmol). The reaction mixture was heated at 50° C. for 2 days. The reaction mixture was then filtered, concentrated and purified with silica gel chromatography with EtOAc:Hexanes=1:8 as the eluent. The product was obtained as a light yellow oil, 67 mg, yield of 48%. HPLC purity: 98.6%. (Retention time: 3.72 min. 40% H$_2$O and 60% MeCN over 30 min at 254 nm on Varian C18 column). $^1$H-NMR (CDCl$_3$): δ 9.63 (s, 1H), 7.21 (d, J=3.48 Hz, 1H), 6.53 (d, J=3.52 Hz, 1H), 4.49 (s, 2H), 3.43 (s, 3H). $^{13}$C-NMR (CDCl$_3$): δ 177.85, 158.47, 152.87, 121.76, 111.26, 66.76, 58.85.

5-(Ethoxymethyl)-2-furan Carboxadehyde (VZHE011)

5-HMF (122 mg, 1.0 mmol) was dissolved in acetonitrile (5 mL), and EtI (3.0 mmol) was added and followed by Cs$_2$CO$_3$ (1.5 mmol). The reaction mixture was heated at 50° C. for 2 days. The reaction mixture was then filtered, concentrated and purified with silica gel chromatography with EtOAc:Hexanes=1:8 as the eluent. The product was obtained as a light yellow oil, 77 mg, yield of 50%. HPLC purity: 95.0%. (Retention time: 4.01 min. 40% H$_2$O and 60% MeCN over 30 min at 254 nm on Varian C18 column). $^1$H-NMR (CDCl$_3$): δ 9.62 (s, 1H), 7.21 (d, J=3.52 Hz, 1H), 6.52 (d, J=3.56 Hz, 1H), 4.54 (s, 2H), 3.60 (q, J=7.00 Hz, 2H), 1.25 (t, J=6.98 Hz, 3H). $^{13}$C-NMR (CDCl$_3$): δ 177.83, 158.95, 152.77, 121.91, 111.08, 66.77, 64.92, 15.19.

5-(Propoxymethyl)-2-furan Carboxadehyde (VZHE 015)

5-HMF (126 mg, 1.0 mmol) was dissolved in acetonitrile (5 mL), and PrI (3.0 mmol) was added and followed by Cs$_2$CO$_3$ (1.5 mmol). The reaction mixture was heated to reflux for 2 days. The reaction mixture was then filtered, concentrated and purified with silica gel chromatography with EtOAc:Hexanes=1:8 as the eluent. The product was obtained as a light yellow oil, 94 mg, yield of 56%. $^1$H-NMR (CDCl$_3$): δ 9.62 (s, 1H), 7.21 (d, J=3.52 Hz, 1H), 6.52 (d, J=3.52 Hz, 1H), 4.54 (s, 2H), 3.49 (t, J=6.68 Hz, 2H), 1.63 (m, 2H), 0.93 (t, J=7.42 Hz, 2H). $^{13}$C-NMR (CDCl$_3$): δ 177.69, 158.93, 152.56, 121.91, 110.90, 72.96, 64.99, 22.82, 10.46.

5-(isopropoxymethyl)-2-furan Carboxadehyde (VZHE016)

5-HMF (126 mg, 1.0 mmol) was dissolved in acetonitrile (5 mL), and i-PrI (3.0 mmol) was added and followed by Cs$_2$CO$_3$ (1.5 mmol). The reaction mixture was stirred at rt for 4 days. The reaction mixture was then filtered, concentrated and purified with silica gel chromatography with EtOAc:Hexanes=1:8 as the eluent. The product was obtained as a light yellow oil, 60 mg, yield of 40%. $^1$H-NMR (CDCl$_3$): δ 9.61 (s, 1H), 7.21 (d, J=3.52 Hz, 1H), 6.52 (d, J=3.52 Hz, 1H), 4.54 (s, 2H), 3.73 (heptet, J=6.12 Hz, 1H), 1.22 (d, J=6.08 Hz, 6H). $^{13}$C-NMR (CDCl$_3$): δ 177.83, 159.57, 152.66, 122.19, 110.83, 72.31, 63.68, 22.11.

5-(tert-Butoxymethyl)furan-2-carbaldehyde (VZHE013)

5-HMF (100 mg, 0.82 mmol) was dissolved in DCM (5 mL), and Boc$_2$O (0.89 g, 4.10 mmol) and Mg(ClO$_4$)$_2$ (36 mg, 0.16 mmol) were added. The reaction mixture was refluxed for 2 days. The reaction mixture was then filtered, concentrated and purified with silica gel chromatography with EtOAc:Hexanes=1:8 as the eluent. The product was obtained as a light yellow oil, 58 mg, yield of 36%. HPLC purity: 95.4%. (Retention time: 4.78 min. 40% H$_2$O and 60% MeCN over 30 min at 254 nm on Varian C18 column). IR: 2974.8, 1676.9, 1188.4, 1019.9, 803.7. $^1$H-NMR (CDCl$_3$): δ 9.59 (s, 1H), 7.20 (d, J=3.48 Hz, 1H), 6.49 (d, J=3.48 Hz, 1H), 4.49 (s, 2H), 1.28 (s, 9H). $^{13}$C-NMR (CDCl$_3$): δ 177.61, 160.33, 152.39, 122.24, 110.30, 74.45, 57.31, 27.47.

5-phenoxymethyl-furan-2-carbaldehyde (5-PMFC)

Phenol (94 mg, 1.0 mmol), chloromethyl furfural (144 mg, 1.0 mmol) were dissolved in DMF (2 mL), and the mixture was cooled to 0° C. Potassium carbonate (170 mg, 1.2 mmol) was then added portion wise. The reaction mixture was stirred at 0° C. to rt for 16 hours. The reaction mixture was diluted with DCM (15 mL), washed with water (3×5 mL), brine (5 mL), dried over Na$_2$SO$_4$, and filtered. The DCM was evaporated under reduced pressure and the crude product was purified by flash chromatography (hexanes/EtOAc 4:1) to give a brownish solid, 130 mg, 64%. M.p.: 81-82° C.

The synthesis of 5-((4-Chlorophenoxy)methyl)furan-2-carbaldehyde (5CMFC) and 5-((2-Nitrophenoxy)methyl)

furan-2-carbaldehyde (5-NMFC) followed the same procedure as 5-phenoxymethyl-furan-2-carbaldehyde.

III. Protection of the Hydroxymethyl and Aldehyde Groups of 5-HMF with Esters (or Ethers) and Thiazolidines, Respectively General Procedure to Prepare Thiozolidines from 5-HMF Esters:

L-Cysteine Ethyl Ester hydrochloride (1.1 mmol) was dissolved in EtOH (2 mL), and triethyl amine (1.1 mmol) was added. The solution was stirred at rt for 10 min. 5-HMF esters or ether in 1 mL of EtOH solution (1 mmol) was added dropwise. The reaction mixture was then stirred at rt for 2 hours. After evaporation, the crude oil was purified through column with EtOAc:Hexanes 1:8 as the eluent.

Ethyl 2-(5-((benzoyloxy)methyl)furan-2-yl)thiazolidine-4-carboxylate (VZHE009)

Yield: 56%. IR: 2980.5, 1717.0, 1094.0, 708.2.
$^1$H-NMR (CDCl$_3$): δ 8.04 (m, 4H), 7.55 (m, 2H), 7.42 (m, 4H), 6.45 (d, J=3.16 Hz, 1H), 6.42 (d, J=3.31 Hz, 1H), 6.40 (d, J=3.16 H, 1H), 6.32 (d, J=3.16 Hz, 1H), 5.81 (s, 1H), 5.59 (s, 1H), 5.29 (s, 2H), 5.27 (s, 2H), 4.25 (m, 4H), 4.17 (t, J=6.50 Hz, 1H), 3.91 (m, 1H), 3.42 (m, 2H), 3.08 (m, 2H), 2.98 (br s, 1H), 2.86 (br s, 1H), 1.31 (t, J=7.09 Hz, 3H), 1.30 (t, J=7.09 Hz, 3H).
$^{13}$C-NMR (CDCl$_3$): δ 171.39, 170.80 (d), 166.33 (2 carbons), 154.80, 151.67 (d), 150.15 (d), 149.83 (d), 133.21, 133.20 (d), 130.08, 130.02 (d), 129.94, 129.92 (d), 128.48 (2 carbons), 111.83 (d), 111.61, 109.28 (d), 108.56, 65.92, 64.74 (d), 64.48, 63.98 (d), 61.88 (d), 61.83, 58.77, 58.64 (d), 38.85 (d), 38.18, 14.28 (2 carbons).

Ethyl 2-(5-(((tert-butoxycarbonyl)oxy)methyl)furan-2-yl)thiazolidine-4-carboxylate (VZHE008)

Yield: 61%. IR: 2980.2, 1734.5, 1369.0, 1251.3, 1155.2, 791.7.
$^1$H-NMR (CDCl$_3$): δ 6.38 (m, 1.8H), 6.34 (d, J=3.26 Hz, 1H), 6.28 (d, J=3.14 Hz, 1H), 5.78 (s, 1H), 5.57 (s, 0.9H), 5.02 (s, 1.8H), 5.00 (s, 2H), 4.26 (m, 2H), 4.25 (n, 1.8H), 4.16 (t, J=6.75 Hz, 1H), 3.90 (m, 0.9H), 3.42 (d, J=7.00 Hz, 0.9H), 3.40 (d, J=6.79 Hz, 1H), 3.07 (dd, J=3.39, 7.00 Hz, 0.9H), 3.06 (dd, J=5.51, 7.00 Hz, 1H), 2.96 (br s, 0.9H), 2.83 (br s, 1H), 1.49 (s, 8.1H), 1.48 (s, 9H), 1.32 (t, J=7.04 Hz, 2.7H), 1.30 (t, J=7.04 Hz, 3H).
$^{13}$C-NMR (CDCl$_3$): δ 171.41, 170.76 (d), 154.93, 153.27 (d), 153.24 (d), 151.74, 149.72 (d), 149.40, 111.92 (d), 111.71, 82.73 (d), 82.66, 65.96, 64.70 (d), 64.48, 63.96 (d), 61.87 (d), 61.82, 60.65, 60.51 (d), 38.86 (d), 38.18, 27.90 (2 carbons), 14.29 (2 carbons).

Ethyl 2-(5-(acetoxymethyl)furan-2-yl)thiazolidine-4-carboxylate (VZHE005)

The synthesis of VZHE005 was carried out as per previously reported procedure (Viil et al., *RSC Advances* 2014, 4, 5689). 5-HMF (126 mg, 1.0 mmol) was dissolved in acetonitrile (5 mL), and MeI (426 mg, 3.0 mmol) was added and followed by Cs$_2$CO$_3$ (488 mg, 1.5 mmol). The reaction mixture was heated at 50° C. for 2 days. The reaction mixture was then filtered, concentrated and purified with silica gel chromatography with EtOAc:Hexanes=1:8 as the eluent. The product was obtained as a light yellow oil, 67 mg, yield of 48%. HPLC purity: 98.6%. (Retention time: 3.72 min. 40% H$_2$O and 60% MeCN over 30 min at 254 nm on Varian C18 column). $^1$H-NMR (CDCl$_3$): δ 9.63 (s, 1H), 7.21 (d, J=3.48 Hz, 1H), 6.53 (d, J=3.52 Hz, 1H), 4.49 (s, 2H), 3.43 (s, 3H). $^{13}$C-NMR (CDCl$_3$): δ 177.85, 158.47, 152.87, 121.76, 111.26, 66.76, 58.85.

Ethyl 2-(5-(methoxymethyl)furan-2-yl)thiazolidine-4-carboxylate (VZHE012)

Yield: 66%. IR: 2981.3, 2932.6, 1733.6, 1189.9, 1086.8, 794.8.
$^1$H-NMR (DMSO-d6): δ 6.44 (d, J=3.20 Hz, 0.5H), 6.38 (d, J=3.16 Hz, 0.5H), 6.34 (m, 2H), 5.70 (d, J=9.56 Hz, 1H), 5.59 (d, J=11.84 Hz, 0.5H), 4.32 (s, 1H), 4.30 (s, 2H), 4.20 (m, 1H), 4.16 (m, 2H), 4.13 (m, 1H), 3.99 (m, 0.5H), 3.82 (t, J=9.42 Hz, 1H), 3.32 (d, J=6.84 Hz, 0.5H), 3.29 (d, J=6.94 Hz, 1H), 3.24 (s, 1.5H), 3.23 (s, 3H), 3.08 (dd, J=8.60, 10.05 Hz, 0.5H), 3.02 (dd, J=5.80, 10.20 Hz, 1H), 1.22 (t, J=7.08 Hz, 3H), 1.21 (t, J=7.08 Hz, 1.5H).
D$_2$O exchange: δ 6.44 (d, J=3.20 Hz, 0.5H), 6.38 (d, J=3.10 Hz, 0.5H), 6.34 (m, 2H), 5.70 (s, 1H), 5.59 (s, 0.5H), 4.32 (s, 1H), 4.30 (s, 2H), 4.20 (m, 1H), 4.16 (m, 2H), 4.13 (m, 1H), 3.99 (t, J=7.69 Hz, 0.5H), 3.32 (d, J=6.84 Hz, 0.5H), 3.29 (d, J=6.87 Hz, 1H), 3.24 (s, 1.5H), 3.23 (s, 3H), 3.08 (dd, J=8.57, 10.06 Hz, 0.5H), 3.02 (dd, J=5.84, 10.31 Hz, 1H), 1.22 (t, J=7.08 Hz, 3H), 1.21 (t, J=7.08 Hz, 1.5H).
$^{13}$C-NMR (DMSO-d6): δ 170.95, 170.56 (d), 154.02, 151.76 (d), 151.50 (d), 151.19 (d), 110.24 (d), 110.09, 108.18 (d), 107.20, 65.43, 65.38 (d), 65.01 (d), 64.51, 64.02 (d), 63.86, 60.96 (d), 60.77, 57.05 (d), 57.02 (d), 37.50, 37.36 (d), 13.97, 17.94 (d).

Hemoglobin Modification, Oxygen Equilibrium and Antisickling Studies Using Human Sickle Blood The twelve compounds, VZHE004, VZHE006, VZHE007, VZHE005, VZHE011, VZHE013, VZHE014, VZHE015, VZHE016, 5-PMFC, 5-CMFC, 5-NMFC, and the parent compound (positive control) 5-HMF were investigated for their abilities to prevent hypoxia-induced RBC sickling (RBC morphology study), increase sickle Hb oxygen affinity (oxygen equilibrium curve; OEC study), and modify sickle Hb (adduct formation study) as previously published (Abdulmalik et al., *Br. J Haematol.*, 2005, 128, 552; Safo et al, *J. Med. Chem*, 2004, 47, 4665). Briefly, blood suspensions from a subject with homozygous SCD (hematocrit: 20%) were incubated under air in the absence or presence of 1, 2 and 5 mM concentration of test compounds at 37° C. for 1 hr to ensure that binding had attained equilibrium. Following, the suspensions were incubated under hypoxic condition (4% oxygen/96% nitrogen) at 37° C. for 2 hr. Aliquot samples were fixed with 2% glutaraldehyde solution without exposure to air, and then subjected to microscopic morphological analysis. The residual samples were washed in phosphate-buffered saline, and hemolyzed in hypotonic lysis buffer for subsequent analyses.

For the OEC study, approximately 100 µl aliquot samples from clarified lysate obtained from the antisickling study were added to 4 ml of 0.1M potassium phosphate buffer, pH 7.0, in a cuvette and subjected to hemoximetry analysis using Hemox™ Analyzer (TCS Scientific Corp.) to assess P$_{50}$ shifts. Finally, for the Hb adduct formation study, clarified lysates, also from the above antisickling study, were subjected to cation-exchange HPLC (Hitachi D-7000 Series, Hitachi Instruments, Inc., San Jose, Calif.), using a weak cation-exchange column (Poly CAT A: 30 mm×4.6 mm, Poly LC, Inc., Columbia, Md.).

Time-Dependent Adduct Formation Studies Using Normal Human Whole Blood

The compounds, VZHE004, VZHE006, VZHE007, VZHE005, VZHE011, VZHE013, VZHE014, VZHE015, VZHE016, 5-PMFC, 5-NMFC, and the control 5-HMF were used to conduct time-dependent studies on Hb adduct formation using normal whole blood. The study was performed in a 96-well deepwell (Thermo Scientific) plate, where each compound at 2 mM concentration was added to 600 μL of whole blood (30% hct) and incubated at 37° C. for 24 hr with shaking (at 140 rpm). At 0.5 hr, 1 hr, 2 hr, 4 hr, 6 hr, 8 hr and 24 hr time intervals, 75 μL aliquot of blood was removed from each well using a multichannel pipette and added to respective tubes containing 75 μL of Na cyanoborohydride and borohydride mix (1:1 v/v 50 mM stock) to terminate the Schiff-base reaction, fix the Schiff-base adducts and reduce the reduce free reactive aldehyde (Davies et al., *Food Chem. Toxicol.* 2009, 47, 1950). We have previously optimized these conditions. After mixing, the tubes were stored immediately at −80° C. until ready for analysis to determine Hb adduct formation using cation-exchange HPLC (Hitachi D-7000 Series, Hitachi Instruments, Inc., San Jose, Calif.).

Crystallization, Data Collection and Structure Determination of liganded Hb in Complex with VZHE004

A freshly made solution of VZHE004 or VZHE005 in DMSO was added to carbon monoxide ligated Hb (30 mg/mL protein) at Hb tetramer-compound molar ratio of 1:10 to form the COHb-compound complex, and then crystallized using 10-20% PEG6000, 100 mM Hepes, pH 7.4. Cherry-red needle crystals formed in 1-3 days for VZHE004 and were used to collect X-ray diffraction data at 100° K using a Molecular Structure Corporation (MSC) X-Stream Cryogenic Cooler System (The Woodlands, Tex.), an R-Axis IV image plate detector, and a Rigaku Micro-Max™-007 generator (40 kV and 20 mA). The crystals were first cryoprotected with 80 μL mother liquor mixed with 62 μL 50% PEG6000. The dataset was processed with the D*trek software (Rigaku) and the CCP4 suite of programs (Winn et al, *Acta Crystallogr. D Biol. Crystallogr.* 2011, 67, 235). The crystal is in the space group $P2_12_12_1$ with cell constant of 62.64, 83.32, and 104.95.

The crystal structure of COHb in complex with VZHE004 was determined by a molecular replacement method with Phenix (Echols et al, *J. Appl. Crystallogr.* 2012, 45, 581; Adams et al, *Methods,* 2011, 55, 94) using the native R2-state Hb crystal structure (PDB code 1BBB) as a search model (Silva et al, *J. Biol. Chem,* 1992, 267, 17248). The structure was refined using both Phenix and CNS (Echols supra; Adams supra; Brunger et al. *Acta Crystallogr. D Biol. Crystallogr.* 1998, 54, 905). The final refined structure at 1.85 Å contained four CO molecules bound at all four distal heme sites, two VZHE004 bound at the a-cleft, and several water molecules with final Rfactor and Rfree of 17.9% and 22.3%, respectively.

Model building and correction were carried out using COOT (Emsley et al. *Acta Crystallogr. D Biol. Crystallogr.* 2010, 66, 486). (The atomic coordinates and structure factor of VZHE004 have been deposited in the RCSB Protein Data Bank with accession code 5URC. Detailed crystallographic and refinement parameters are reported in Table 2. Coordinates for the structure of VZHE004 in complex with carbon monoxide hemoglobin have been deposited in the Protein Data Bank with the accession code 5URC.

Results

Novel Derivatives Modified Hb and Increased its Affinity for Oxygen with Homozygous Sickle Blood Aromatic aldehydes that modify Hb and increase the protein affinity for oxygen are expected to prevent hypoxia-induced polymerization with concomitant RBC sickling. Thus, all compounds were tested for their effect on Hb modification and Hb oxygen affinity at 1 mM, 2 mM and 5 mM as previously reported,[18,19] and the results summarized in Table 1 (for the 2 mM drug concentration), and FIGS. 2 and 3 (for all concentrations). We observed a concentration-dependent effect on Hb S modification (FIG. 2a-c) and Hb oxygen affinity ($P_{50}$ shift) (FIG. 3A-C). For the majority of compounds, across all three groups—the esters VZHE004, VZHE006, VZHE007; the alkyl ethers VZHE005, VZHE011, VZHE015, VZHE016; and the aryl ether 5-PMFC—there appears to be a direct correlation between the two critical biochemical effects. With few exceptions, most of the derivatives, including VZHE004, VZHE006, VZHE007, VZHE005, VZHE011, VZHE015, VZHE016, and 5-PMFC exhibited similar or greater Hb modification and $P_{50}$ shift than 5-HMF, especially at the lower concentrations of 1 and 2 mM. On the other hand, 5-NMFC and 5-CMFC which though either showed better than, or comparable adduct formation to 5-HMF, respectively, unexpectedly resulted in significantly less $P_{50}$ shift than 5-HMF at all three concentrations (Table 1, FIGS. 2C and 3C). This observation (would be further discussed) is likely due to binding of the compounds to both liganded and unliganded Hb, which could lead to stabilization of R-state and/or T-state Hb affecting the direction and magnitude of the $P_{50}$ shift.

TABLE 1

Hemoglobin adduct formation, oxygen equilibrium, and antisickling studies using homozygous sickle red blood cells at 2 mM test compound concentration[a]

| Compound | Modified Hb (%)[b] | $\Delta P_{50}$ (%)[c] | Inhibition of Sickling (%)[d] |
|---|---|---|---|
| 5-HMF | 32.8 ± 1.6 | 33.4 ± 0.9 | 25.7 ± 4.4 |
| Ester Derivatives | | | |
| VZHE004 | 43.5 ± 8.4 | 44.6 ± 11.9 | 26.3 ± 4.4 |
| VZHE006 | 50.0 ± 3.0 | 44.8 ± 12.9 | 71.6 ± 0.1 |
| VZHE007 | 44.5 ± 6.0 | 38.9 ± 11.9 | 10.0 ± 5.9 |
| VZHE014 | 19.7 ± 6.3 | 35.7 ± 8.1 | 8.4 ± 5.9 |
| Alkyl Ether Derivatives | | | |
| VZHE005 | 35.3 ± 11.6 | 39.4 ± 8.3 | 35.3 ± 6.1 |
| VZHE011 | 40.4 ± 3.9 | 39.8 ± 0.8 | 58.8 ± 7.0 |
| VZHE013 | 15.7 ± 4.3 | 24.0 ± 5.6 | 7.4 ± 6.9 |
| VZHE015 | 39.7 ± 8.2 | 44.0 ± 9.7 | 62.9 ± 6.2 |
| VZHE016 | 36.4 ± 9.7 | 38.4 ± 10.4 | 22.5 ± 8.8 |
| Aryl Ether Derivatives | | | |
| 5-NMFC | 40.5 ± 17.6 | 13.4 ± 5.7 | 10.3 ± 0.5 |
| 5-PMFC | 60.53 ± 5.3 | 45.4 ± 14.6 | 94.7 ± 0.1 |
| 5-CMFC | 26.7 ± 6.5 | 13.2 ± 5.2 | 2.0 ± 1.9 |

[a]All studies were conducted with SS cells suspensions (20% hematocrit) incubated with 2 mM of each test compound; and the results are the mean values ± SD for three separate experiments (biological replicates). The final concentration of DMSO was <2% in all samples, including in control samples. [b]Hb S adduct values obtained from HPLC elution patterns of hemolysate after incubation of compounds with SS cells. [c]$P_{50}$ is the oxygen pressure at which the hemolysates are 50 % saturated with oxygen. $\Delta P_{50}$ (%) was determined as:

$$\Delta P_{50}(\%) = \frac{P_{50} \text{ of lysates from untreated cells} - P_{50} \text{ of lysates from treated cells}}{P_{50} \text{ of lysates from untreated cells}} \times 100$$

[d]Antisickling studies with SS cells (20 % hematocrit) were conducted under hypoxia (4% Oxygen/96% Nitrogen).

Figure 2A:
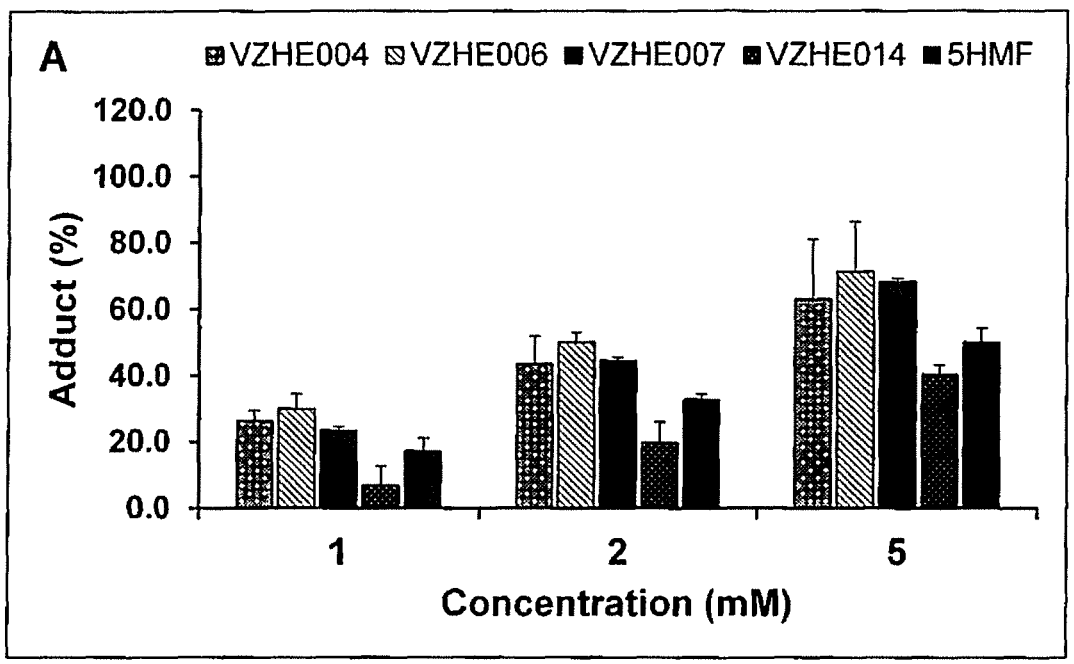
FIG. 2A-C. Concentration-dependent modification of Hb S by test compounds. Most ester and alkyl ether derivatives demonstrated similar or higher levels of modification (HbS adducts) as 5-HMF (A, B). The two aryl ether derivatives 5-((2-nitrophenoxy)methyl)-2-furan carbaldehyde (5-NMFC) and 5-(phenoxymethyl)-2-furan carbaldehyde (5-PMFC), especially the latter showed superior Hb modification at all three experimental concentrations (C).
Figure 2B:
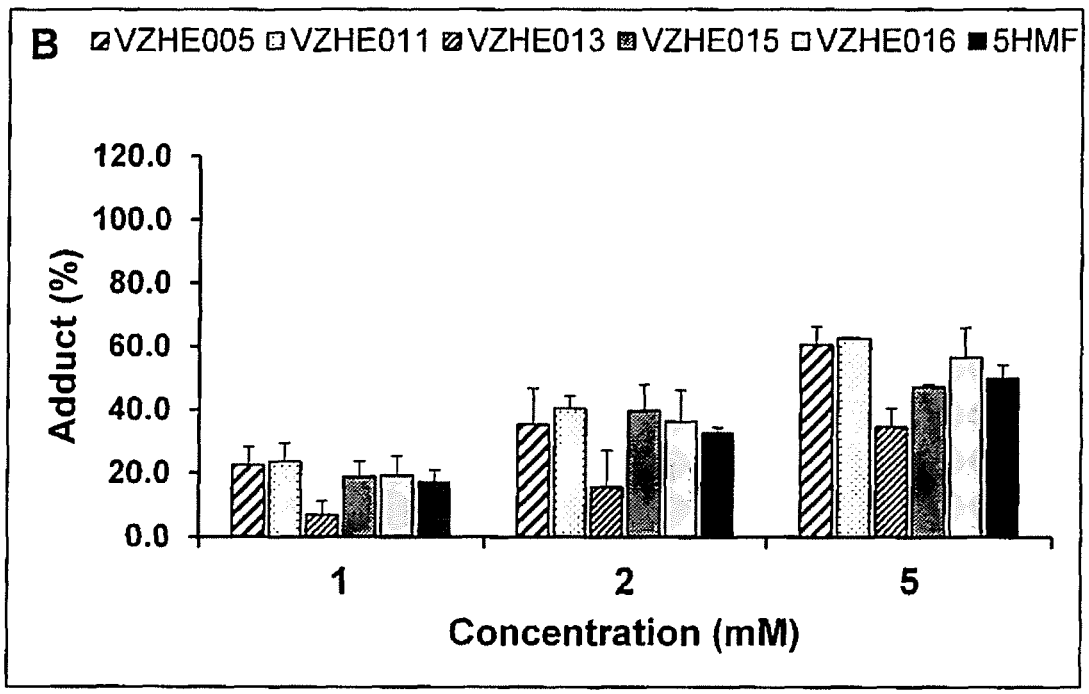
Figure 2C:
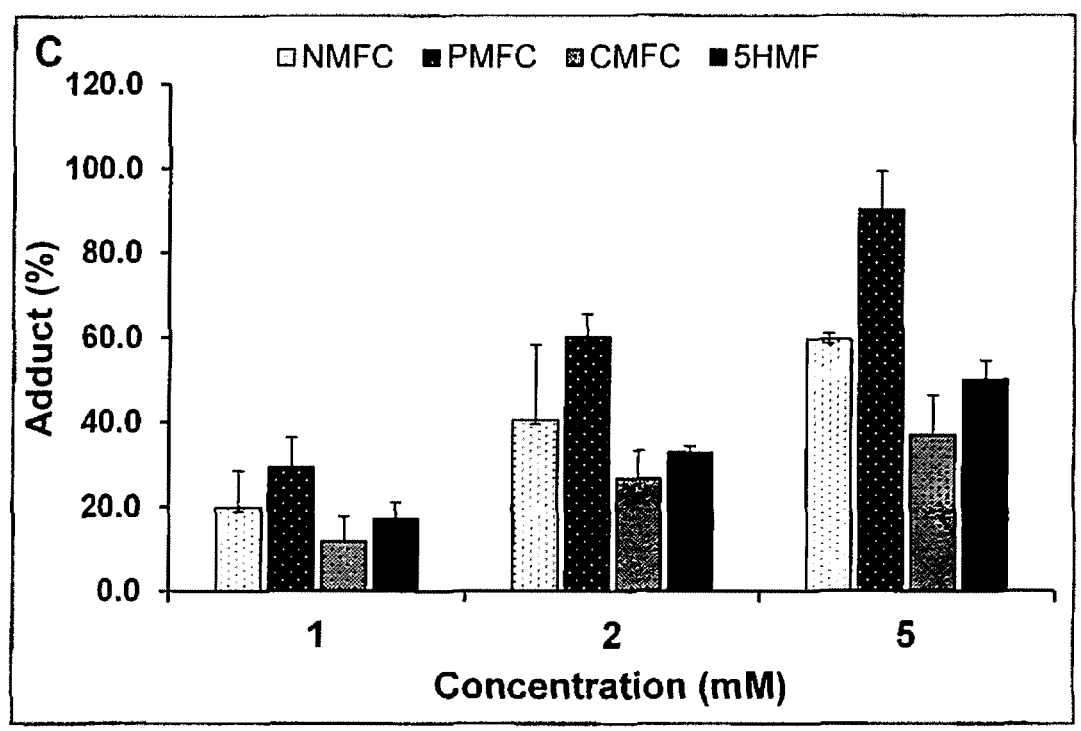
Figure 3A:
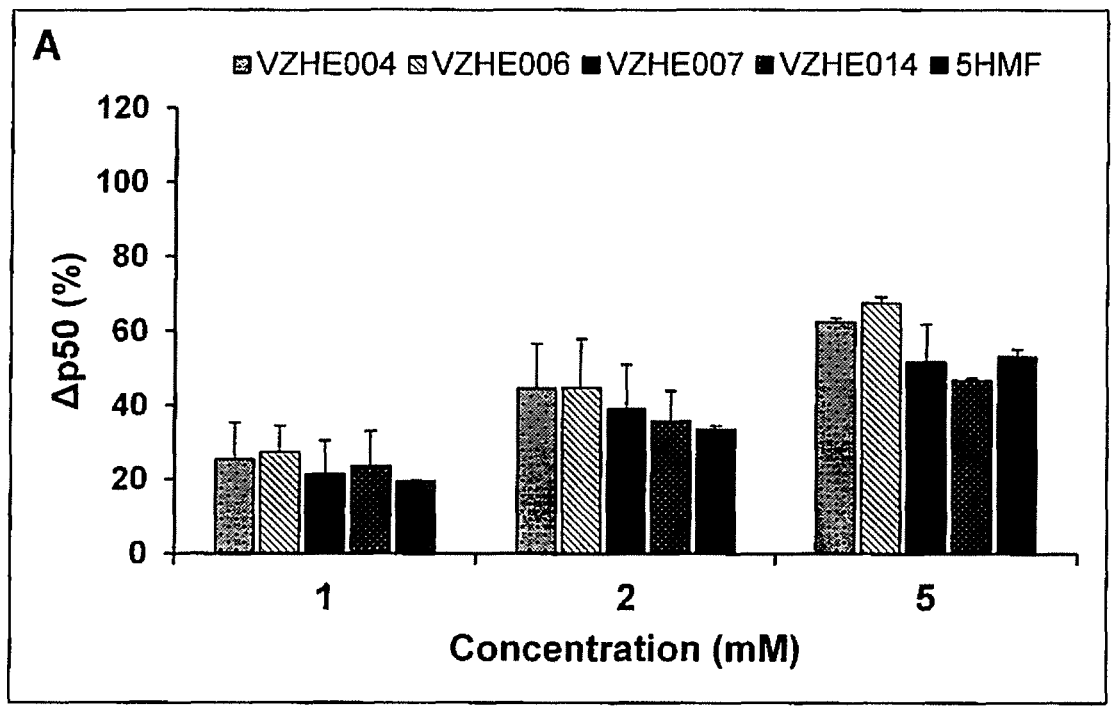
FIG. 3A-C. Degree of shift in oxygen equilibra ($\Delta P_{50}$) by test compounds. In accordance with observations on the levels of Hb modification, both ester and alky ether derivatives showed similar or slight improvements of $P_{50}$ shift over 5-HMF (A, B). The aryl ether 5-PMFC showed better $P_{50}$ sift than 5-HMF, while the other two aryl ethers 5-NMFC and 5-((4-chlorophenoxy) methyl)-2-furan carbaldehyde (5-CMFC) showed lower degrees of shift than 5-HMF (C).
Figure 3B:
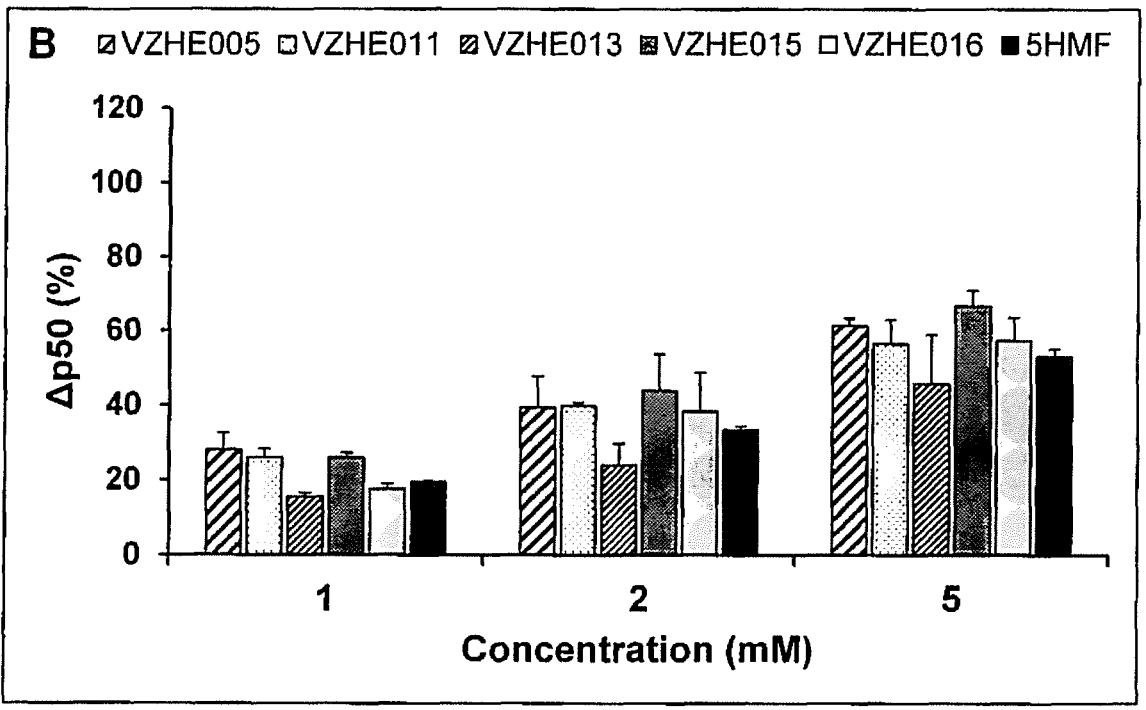
Figure 3C:
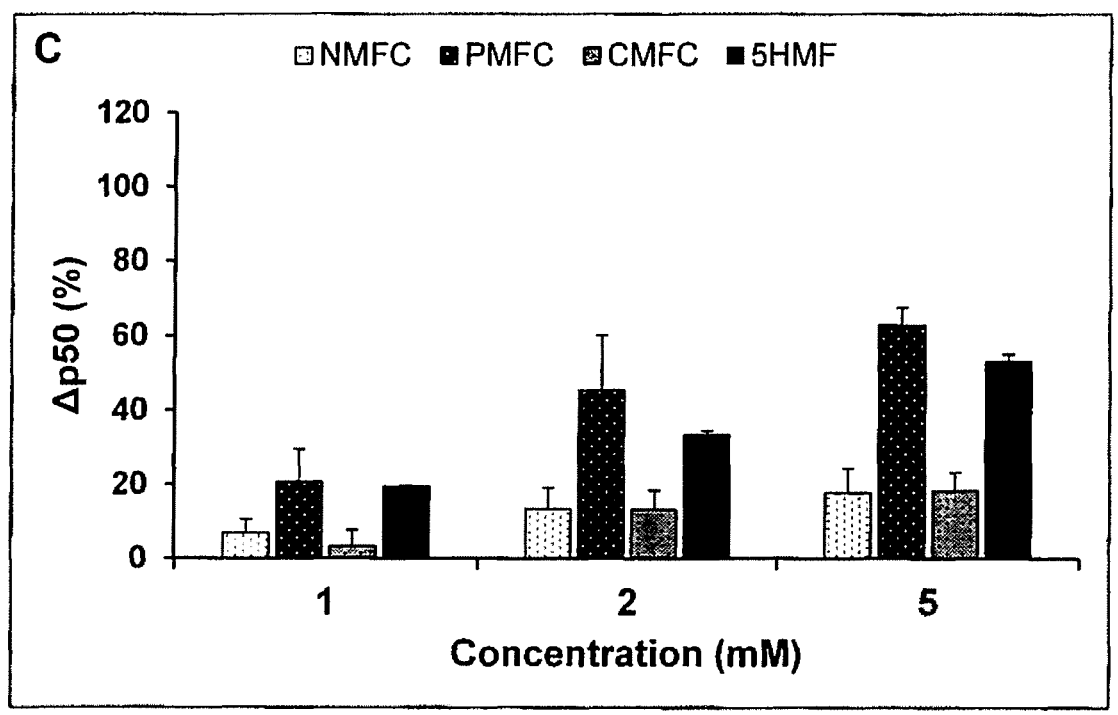

Among the esters, VZHE004, VZHE006 and VZHE007 exhibited similar and significantly higher adduct formation than the phosphate ester VZHE014 (Table 1, FIG. 2A). Nonetheless, all four compounds showed potent $P_{50}$ shifts that are similar or slightly better than 5-HMF (Table 1, FIG. 3A). With the exception of the ethyl ether VZHE013 which showed weaker adduct formation and $P_{50}$ shift than 5-HMF, the other four ethers VZHE005, VZHE011, VZHE015 and VZHE016 were comparable or slightly more potent than 5-HMF (Table 1, FIGS. 2B and 3B). In both the ester and alkyl ether class of compounds, there appears to be no correlation between the substituent size and activity. In the aryl ethers, 5-PMFC without any substitution on the phenyl ring is significantly more potent in modifying Hb or increasing Hb affinity for oxygen than the analogs 5-CMFC and 5-NMFC with chloro- or nitro-substitution, respectively (Table 1, FIGS. 2C and 3C).

Novel Derivatives Demonstrated Improved In Vitro Antisickling with Homozygous Sickle Blood To investigate whether improvement in Hb oxygen affinity by several of the compounds also translated to their ability to prevent RBC sickling, all twelve compounds and 5-HMF were subjected to an in vitro sickling assay under hypoxic conditions using SS blood from SCD patients as previously described (Abdulmakik, supra; Safo, supra). The results of the antisickling study (using aliquot samples from the same incubation assay for determining Hb adduct and OEC shifts) demonstrated in most part a dose-dependent inhibition of RBC sickling (FIGS. 4 and 5), consistent with the primary mechanism of action, i.e., by modifying Hb and increasing the protein affinity for oxygen. At the lowest concentration of 1 mM, almost all compounds, including 5-HMF showed only minimal antisickling effect, except 5-PMFC, which inhibited RBC sickling approximately 17% (FIGS. 4 and 5). At 2 mM concentration, the ester VZHE006, the three alkyl ethers VZHE005, VZHE011 and VZHE015, and the aryl ether 5-PMFC showed significant antisickling potency (35-95% RBC sickling inhibition) when compared to 5-HMF (26%), with 5-PMFC showing the most potent effect of ~95% sickling inhibition (Table 1, FIGS. 4 and 5). At 5 mM concentrations, more than half of the compounds inhibited over 95% RBC sickling; exception being VZHE004 (60%), VZHE014 (43%), VZHE016 (<10%), 5-NMFC (<10%) and 5-CMFC (<10%) (FIGS. 4 and 5). The observation that no significant antisickling activity was observed at 1 mM for most of the compounds even though they significantly increased Hb affinity for oxygen suggests that a certain threshold of $P_{50}$ shift is required for antisickling effect to manifest. As expected from their minimal effect on Hb oxygen affinity, 5-NMFC and 5-CMFC ($P_{50}$ of <20 mmHg) showed almost no antisickling effect (<10%) at all three doses (Table 1, FIGS. 4C and 5C). What is most surprising is that VZHE013, which showed % $P_{50}$ shifts of 16, 24 and 46 at 1, 2 and 5 mM (FIG. 3B), respectively and expected to translate into significant antisickling effect showed less than 5% sickling inhibition at all three concentrations (Table 1, FIGS. 4B and 5B). The explanation behind this observation is not clear.

Figure 4A:
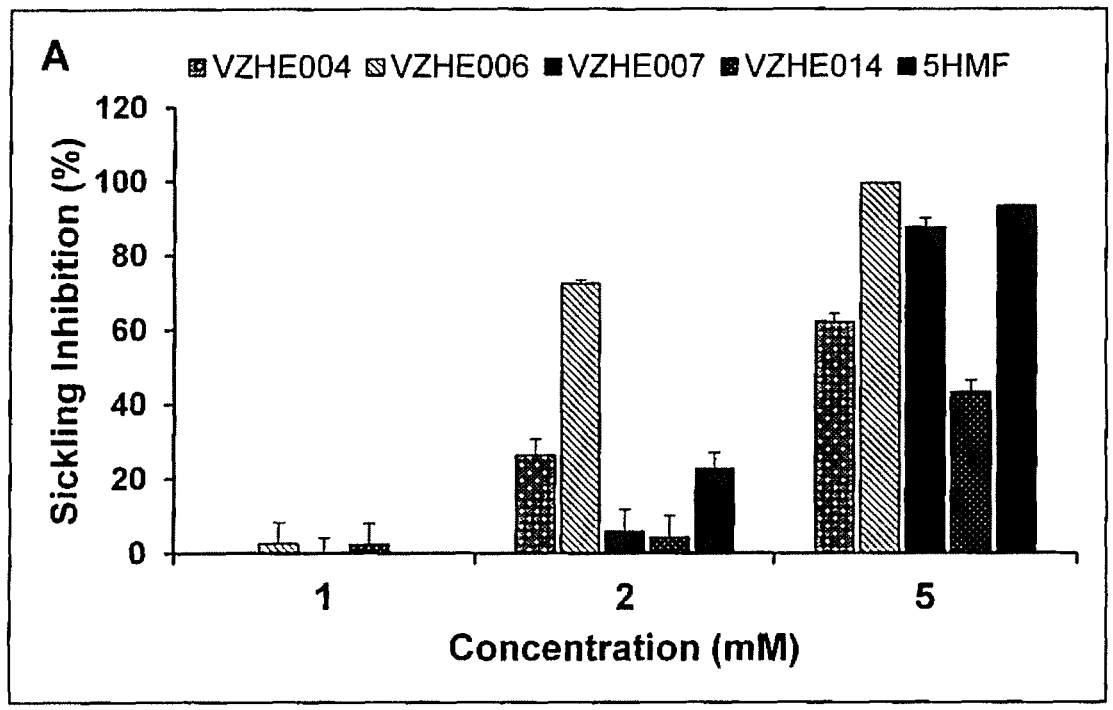
FIG. 4A-C. Inhibition of SS cell sickling by test compounds. Representatives from all three groups of compounds demonstrated improved reduction of SS cell sickling compared to 5-HMF. Among the ester derivatives, tert-Butyl ((5-formylfuran-2-yl)methyl) carbonate (VZHE006) showed remarkable (~3-fold) improvement over 5-HMF at 2 mM concentrations (A). Among the alkyl ethers VZHE011 and VZHE015 were superior at 2 mM concentration (B). Among the aryl ethers, 5-PMFC attained maximum effect at 2 mM concentration, while 5-NMFC and 5-CMFC barely showed any antisickling effect even at 5 mM concentration. (C). The following compounds VZHE007, VZHE014, VZHE013, 5-NMFC and 5-CMFC from all three groups showed poor antisickling effects (A, B, C).
Figure 4B:
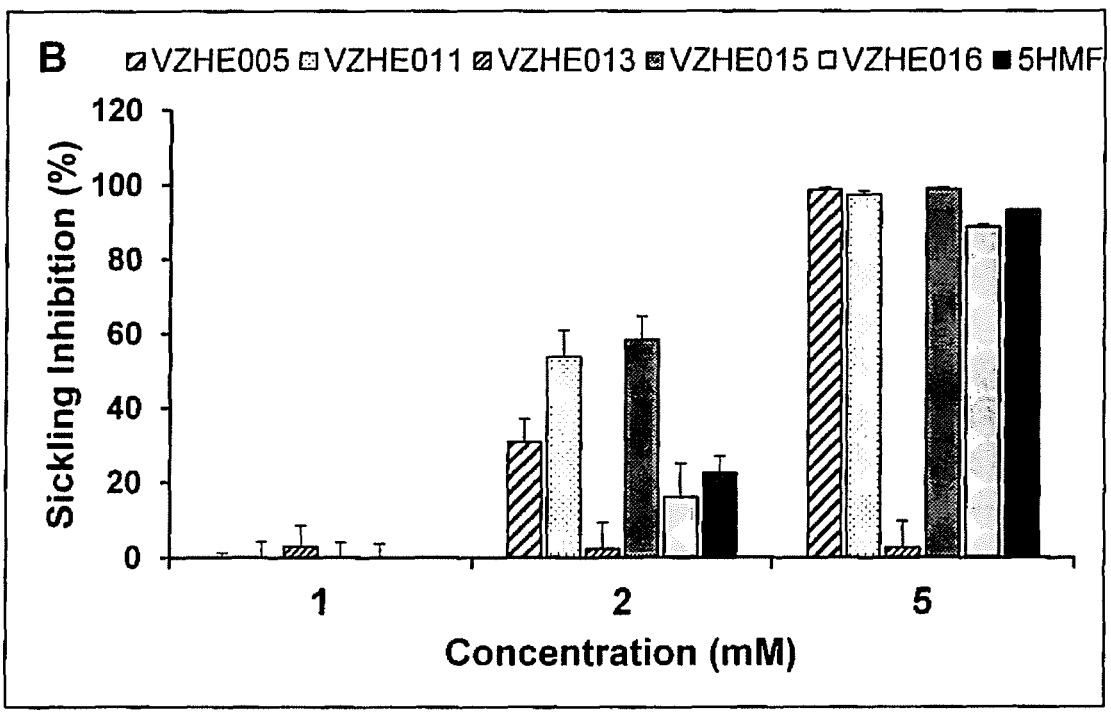
Figure 4C:
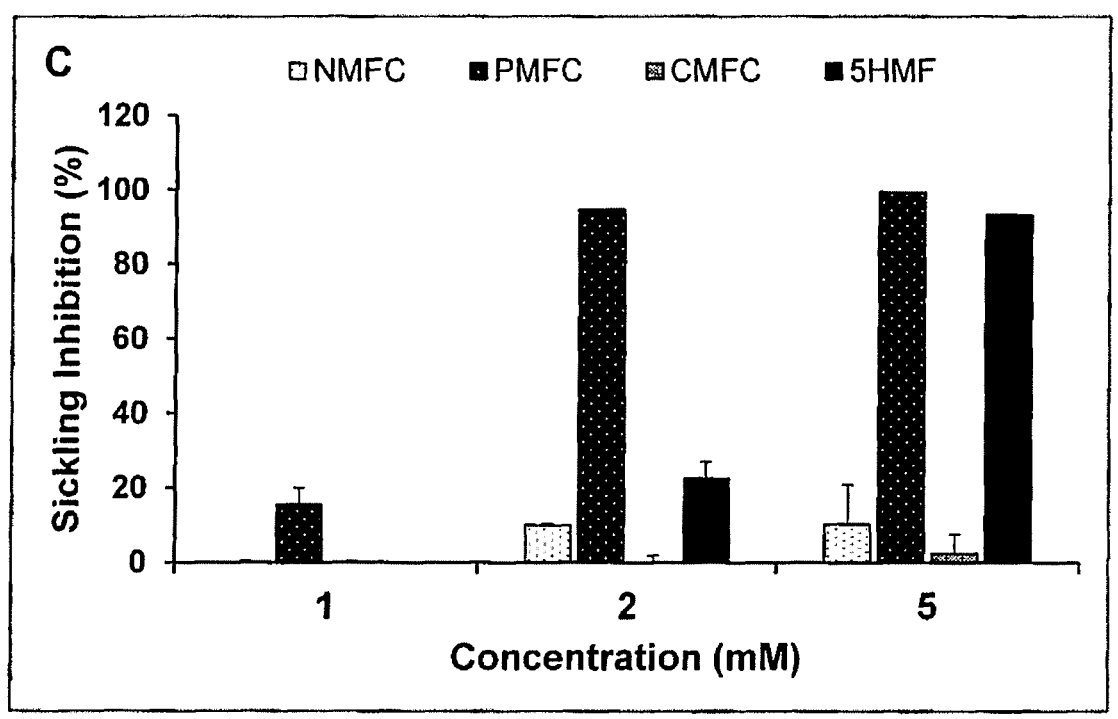
Figure 5A:
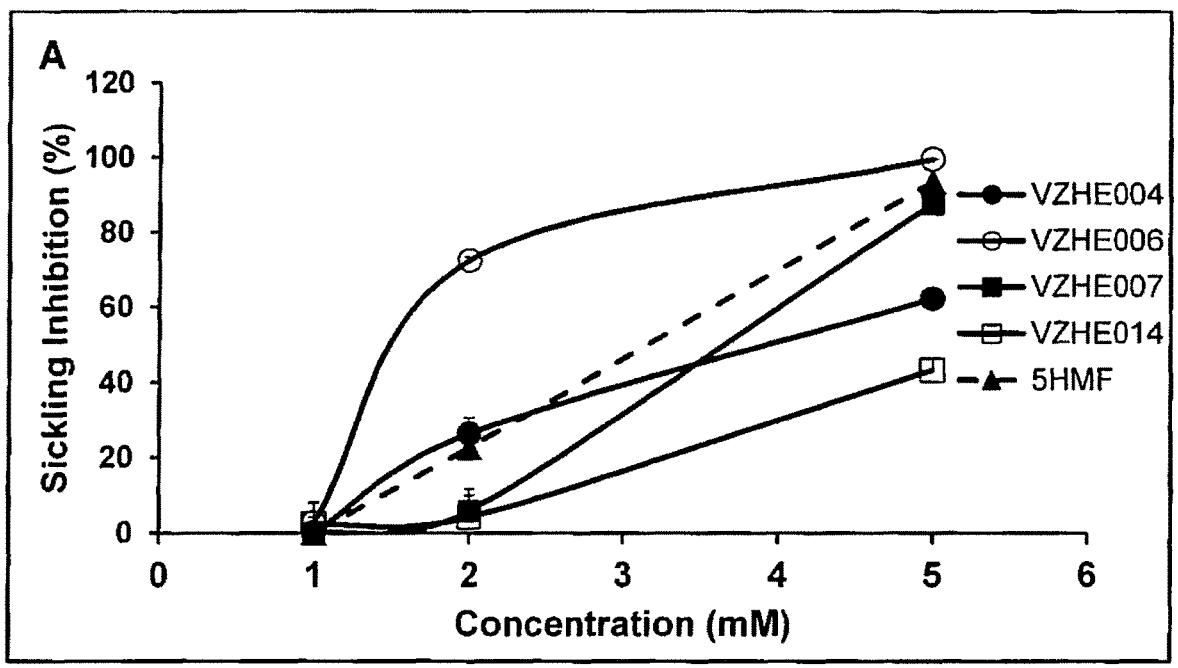
FIG. 5A-C. Line charts showing dose-dependent inhibition of SS cell sickling from experiments reported in FIG. 4. The superior effects of VZHE006 (A) and 5-PMFC (C) over 5-HMF (dotted lines) are clearly demonstrated at 2 mM concentrations. Improved properties of VZHE011 and VZHE015 are also shown (B).
Figure 5B:
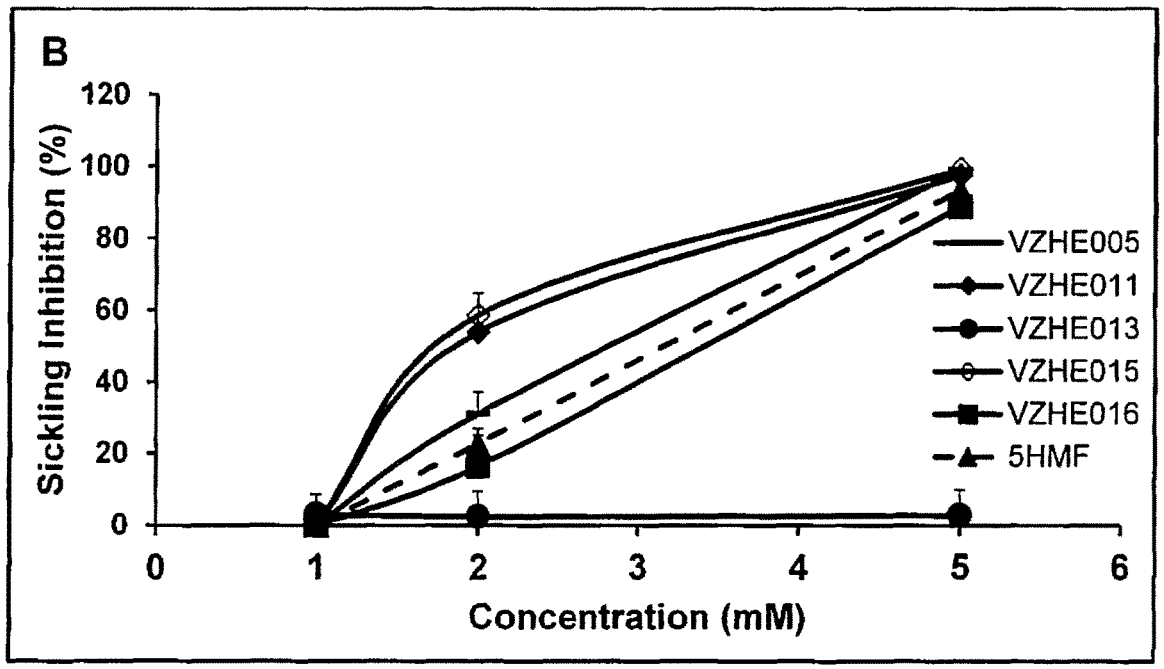
Figure 5C:
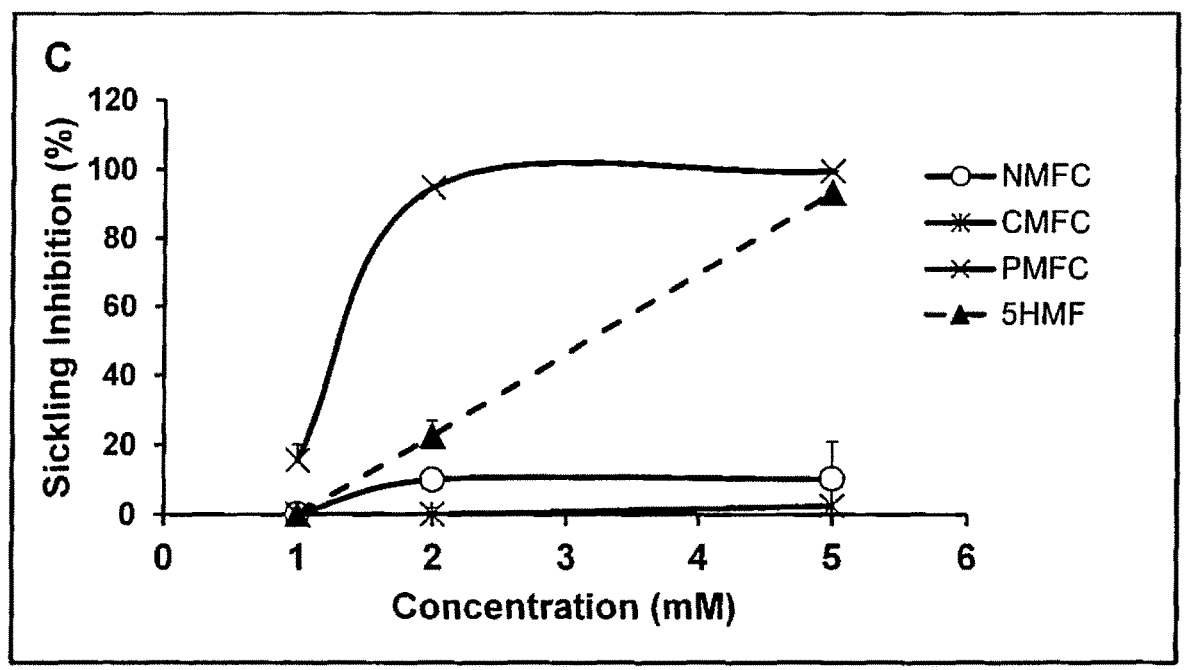

Although the $P_{50}$ shifts of the esters VZHE004, VZHE006, VZHE007 and VZHE014 are comparable, VZHE006 exhibits roughly 3-fold antisickling potency over the other three esters and 5-HMF at 2 mM concentration (Table 1, FIGS. 4A and 5 A). At 5 mM, VZHE006 remains the most potent (>95%), followed by VZHE007 at ~83%, and then VZHE004 (~60%) and VZHE014 (~40%) (Table 1, FIGS. 4 A and 5 A). These observations may be due to dual mechanism of antisickling effect that involve increasing the oxygen affinity of Hb, as well as direct stereospecific polymer destabilization.

Among the alkyl ethers, with the exception of VZHE013, which showed very little antisickling activity at all concentrations, the rest exhibited over 95% antisickling effect at 5 mM (Table 1, FIGS. 4B and 5B). At 2 mM concentration, VZHE011 and VZHE015 are more potent (>54% inhibition) than 5-HMF (~23%), VZHE005 (~31%) and VZHE016 (~16%). Like, the esters, there appears to be no direct correlation between structure and antisickling activity of the alkyl ether class of compounds.

Within the aryl ethers, 5-PMFC exhibits the most potent antisickling effect (~95% vs ~23% by 5-HMF at 2 mM), while 5-CMFC and 5-NMFC with substitution on the phenyl ring were among the least potent compounds (<10%) (Table 1, FIGS. 4C and 5C). The fact that 5-CMFC and 5-NMFC show significant adduct formation but very little $P_{50}$ shifts and antisickling activities highly suggest that these compounds not only bind to liganded Hb and stabilize the R-state, but also bind to unliganded Hb and confer significant stability to the T-state that ultimately led to a smaller increase in Hb affinity for oxygen. To fully understand the effect of substitution on the aryl ring of these ethers on Hb allosteric activity would require extensive SAR studies in the future.

An important observation is that the compounds display different antisickling profiles with increasing concentration (FIG. 5). 5-HMF and the ether derivatives VZHE005 and VZHE016 show linear relationships between sickling inhibition and the compounds' concentration in the medium. Similar observation has previously been reported for 5-HMF.[18]. Impressively, the aryl ether 5-PMFC and the ester VZHE006 show very rapid antisickling effect when the concentration is increased from 1 mM to 2 mM, leveling off to almost ~100% RBC inhibition, although slower for VZHE006. Thus, these two compounds, especially 5-PMFC are capable of eliciting maximum antisickling effect at the relatively low compound concentration of 2 mM or even less. Other derivatives, such as VZHE011 and VZHE013 also show similar antisickling profile as VZHE006 but with significantly slower rate of RBC inhibition from 1 mM to 2 mM (FIG. 5). The esters VZHE007 and VZHE014 on the other hand show a lag in antisickling effect from 1 mM to 2 mM, and only after 2 mM elicit any significant biological effect (FIG. 5). The other compounds, the alkyl ether VZHE013, and the aryl ethers 5-NMFC and 5-CMFC barely showed any antisickling activity over the range of the three concentrations (FIG. 5). This observation, taken in conjunction with the adduct formation and $P_{50}$ shift results, as noted above, clearly suggests multiple mechanisms of antisickling action by these compounds.

Aryl Ethers Showed Improved In Vitro Metabolic Profile

Figure 6A:
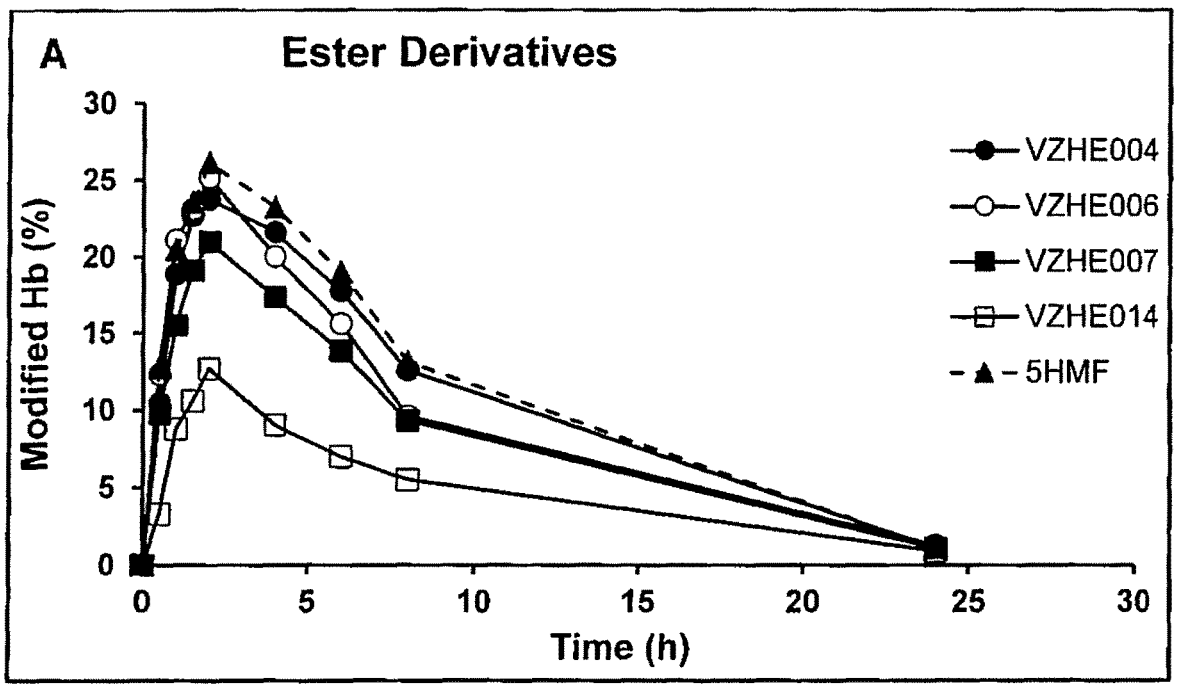
FIG. 6A-C. Time-dependent modification of Hb A in normal blood incubated with test compounds. Levels of modified Hb peaked between 2-4 h for all compounds followed by a decline, suggesting that the compounds are subject to metabolism by RBC enzymes. For the esters and alkyl ethers, there was similar decline in adduct formation at 24 hrs as 5-HMF (A,B), while the aryl ethers showed slower decline (C).
Figure 6B:
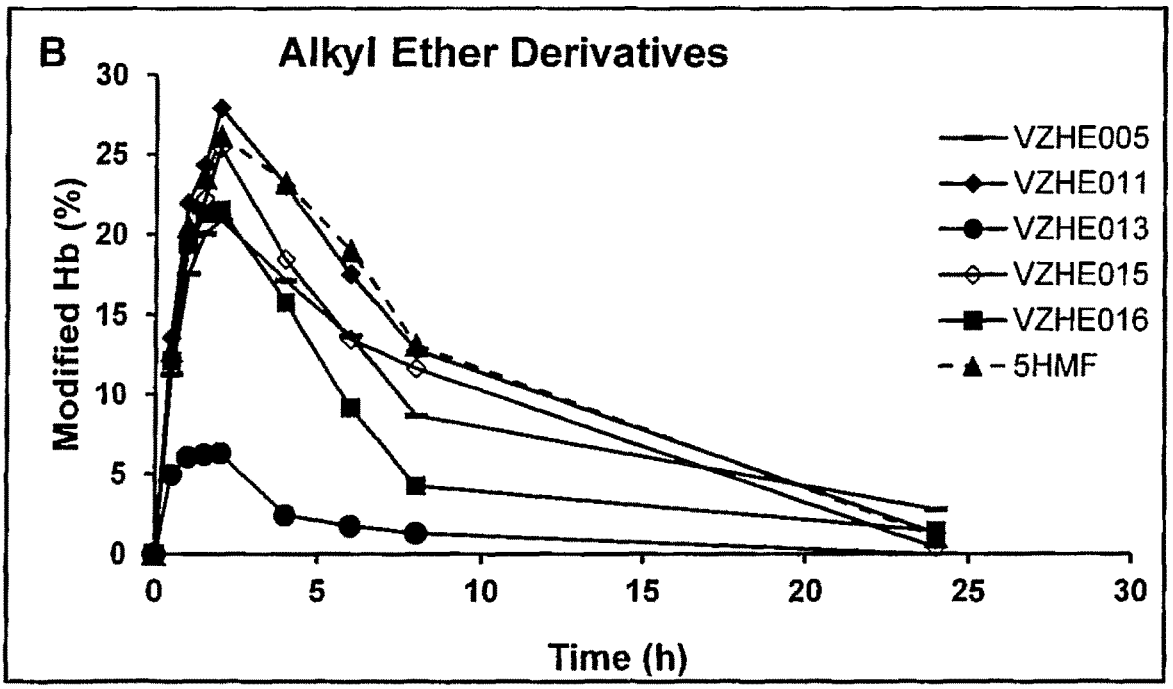
Figure 6C:
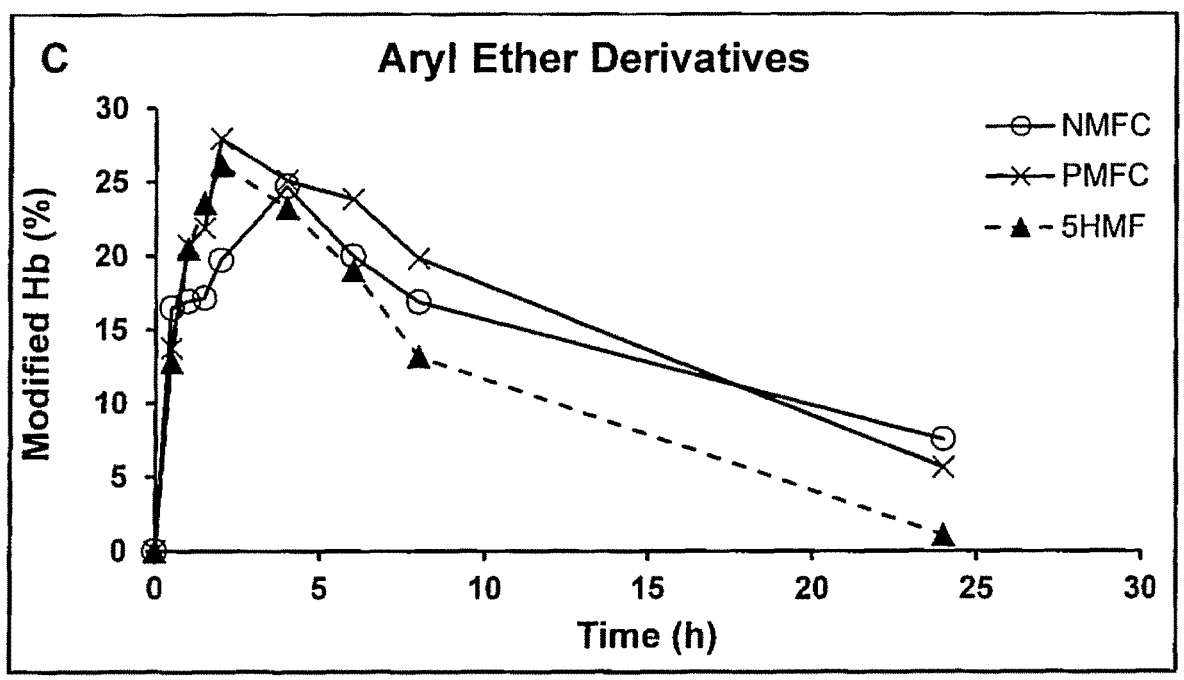

One of the goals was to improve on the antisickling potency of 5-HMF which we seem to have accomplished to some extent. As noted above, 5-HMF suffers from oxidative metabolism that leads to short half-life and suboptimal bioavailability. Thus, a second goal was to improve on the pharmacokinetic properties of 5-HMF through derivatization to reduce the apparent rapid oxidative metabolism of the aldehyde into the inactive acid analog. We therefore conducted in vitro time-dependent Hb modification studies with the derivatives (2 mM drug concentration) using freshly drawn normal whole blood to determine whether the structural modifications, in addition to the observed improved functional/biological activity, have also translated into improvement in the compounds duration of action. Blood contains enzymes that are known to metabolize aromatic aldehydes into their corresponding non-active acid analogs, and is a good predictor of the metabolic stability of aromatic aldehyde. The result shows all compounds to exhibit maximum Hb modification at 2-4 hrs and then declined toward the baseline during the 24-hour experiment (FIG. 6). With the exception of the aryl ethers (5-NMFC and 5-PMFC), all other compounds (esters and alkyl ethers) showed similar metabolic profile in whole blood as 5-HMF suggesting that derivatization of 5-HMF with aryl substituent at the alcohol position is most optimal for decreasing metabolism of 5-HMF in blood. It is expected that prodrugs or derivatives of 5-HMF with aryl substituents at the alcohol position not only will exhibit improved potency but also extended (longer) pharmacologic effects. Nonetheless, the esters and alkyl ethers due to their improved potency over 5-HMF should also translate into better pharmacologic compounds.

Structural Study Showed VZHE004 Binds to the α-Cleft of Hemoglobin

Based on 5-HMF's mode of binding to liganded Hb, we structurally modified the lead compound VZHE004 into several derivatives that could increase further interactions with Hb. Successful crystallization experiments for VZHE004 and VZHE005 with liganded Hb permitted determination of the crystal structure of VZHE004 in complex with CO-liganded Hb in the R2-state conformation. The structure was solved using molecular replacement with the native R2-state Hb structure (PDB code 1BBB) and refined to 1.85 Å. Structural statistics are summarized in Table 2, and the structure deposited in the Protein databank (PDB) with the ID code 5URC.

Figure 7A:
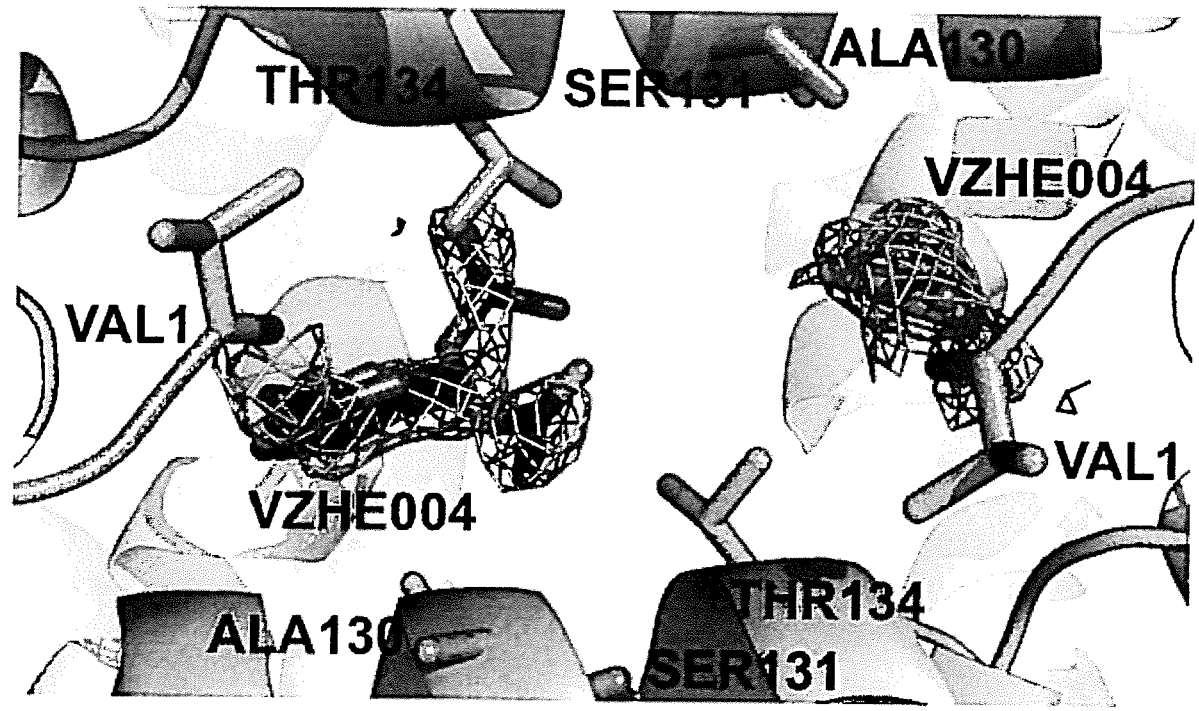
FIG. 7A-B. Crystal structure of carbon monoxide Hb in complex with VZHE004 in the R2-state conformation. Hb subunits are in sticks or ribbons (α1-subunit in cyan, α2-subunit in magenta, β1-subunit in yellow, and β2-subunit in white). (A) A pair of VZHE004 molecules (blue and green sticks) bound at the α-cleft of Hb making Schiff-base interactions with the αVal1N. Superposed on the bound VZHE004 is the final electron-density map with coefficients 2Fo-Fc shown at 0.6σ level. Note that the compound was refined as 5-HMF at the α1Val1 site, while the full VZHE004 was modelled at the α2Val1 binding site but with the methyl acetate refined in two alternate conformations. (B) VZHE004 and 5-HMF superposed on each other showing similar binding modes.
Figure 7B:
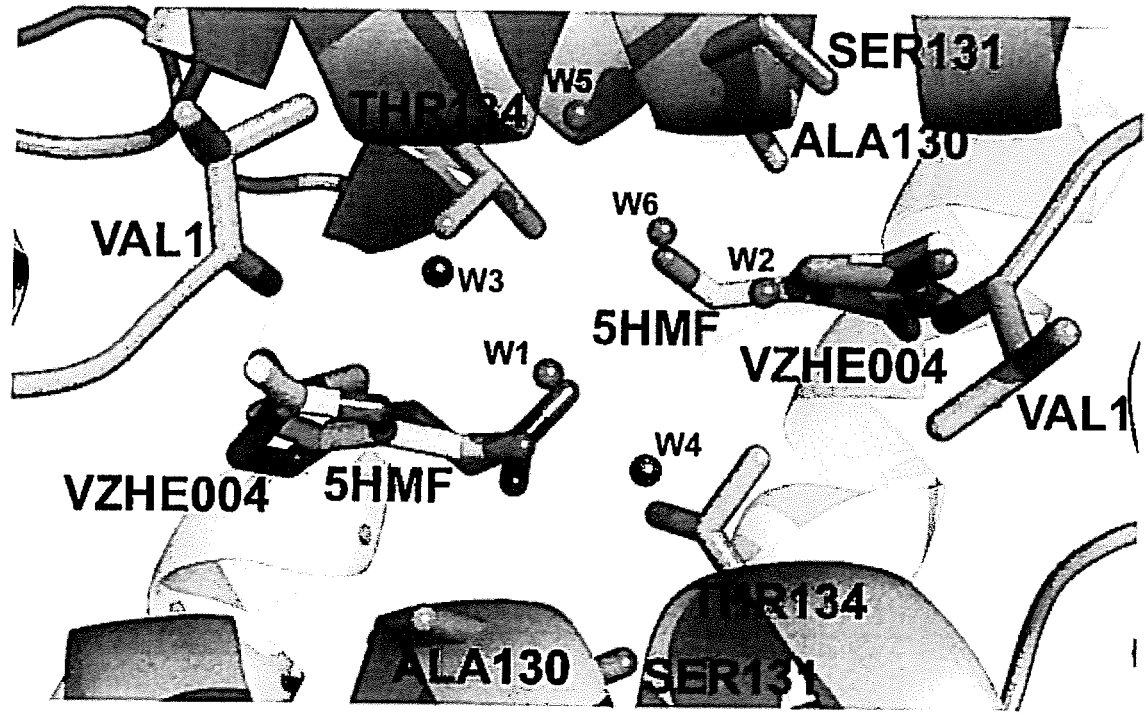

The overall tetrameric structure is indistinguishable (rmsd ~0.4 Å) from 1BBB or the R2 structure in complex with 5-HMF (PDB code 1QXE). Like 5-HMF we also observed a pair of VZHE004 molecules covalently bound to the N-terminal αVal1 amines (Schiff-base interaction) in a symmetry-related fashion at the α-cleft (FIG. 7). The electron density of VZHE004 was relatively weak especially at the methyl acetate position. As such, the compound was refined as 5-HMF at the α1Val1 site, while the full VZHE004 was modelled at the α2Val1 binding site but with the methyl acetate refined in two alternate conformations (FIG. 7a). However, to make sure that the disorder is not due to partial hydrolytic cleavage of the ester, Hb and VZHE004 were incubated for three days. The UPLC-MS analysis of the incubated solution showed intact VZHE004, suggesting that the observed electron density is likely due to disorder.

A hallmark of 5-HMF binding is a direct and/or water-mediated hydrogen-bond interactions that involve the 5-hydroxyl oxygen or the furan oxygen with the protein, which in addition to the Schiff-base interaction explain the potent functional and antisickling activities of 5-HMF. The present structure comparative analysis showed that VZHE004 and 5-HMF bind and make similar interactions with the R2 liganded Hb that tie the two α-subunits together through direct and/or hydrogen-bond interactions with the hydroxyl of αThr134 and αSer131 (FIG. 7), providing an atomic level explanation of the compounds ability to increase Hb affinity for oxygen. The methyl acetate moiety appears to make hydrophobic interactions with αAla130, αSer131, and αThr134, however the apparent disorder suggest these interactions to be weak. It is likely that the other derivatives bind similarly.

Discussion

Based on the binding mode of 5-HMF to liganded Hb, it was hypothesized that derivatization might lead to further interactions with the protein that could potentially enhance its functional and biological effect. The results showed that the compounds bind to Hb, resulting in modification and increasing oxygen affinity of the protein with concomitant inhibition of RBC sickling. Importantly, several of the compounds including VZHE005, VZHE011, VZHE006, VZHE015, and 5-PMFC at 2 mM showed a 1.5-to 4.0-fold improvement in antisickling activity compared to 5-HMF, with 5-PMFC being the most potent, reaching almost 95% potency compared to the ~26% by 5-HMF at 2 mM (Table 1). It is also worth pointing out that 5-PMFC, as well as VZHE006, VZHE011 and VZHE015 to varying extents, are capable of eliciting a significant antisickling effect at relatively low concentrations (FIG. 5).

The superior functional and/or antisickling activity of several of these compounds when compared to 5-HMF could in part be due to the additional protein interactions afforded by the alcohol substituents (with αAla130, αSer131 and αThr134) as suggested by the crystal structure of Hb in complex with VZHE004.

The antisickling activity of aromatic aldehydes is primarily due to Schiff-base interactions between the aldehyde moiety and the N-terminal αVal1 amines of Hb. Competing with this reaction are several enzymatic reactions; principally metabolism of the aldehyde into the pharmacologically inactive acid, such as by aldehyde dehydrogenase, aldehyde oxidase in the liver, blood and other tissues. This is especially true for 5-HMF, which undergoes extensive oxidative metabolism that reduces its pharmacologic effect. By derivatizing 5-HMF, improvement in the compounds' pharmacokinetic properties was theorized due to decreasing metabolism of the aldehyde moiety. However, it appears that like 5-HMF, the esters and alkyl ethers regardless of the substitution at the 5-hydroxyl position also show similar metabolic profile as 5-HMF in whole blood (FIG. 6). Although, not yet tested, other metabolic routes, including the liver would also play a role in metabolizing these compounds. The aryl ethers, as shown by 5-PMFC and 5-NMFC exhibit some resistance to metabolism, suggesting that aryl ethers, at least in blood, may afford better protection against oxidative metabolism. Additionally, 5-PMFC also showed the most potent antisickling effect.

CONCLUSION

In this study, we demonstrate that derivatization of 5-HMF has led to newer generation of analogs with greater potency and/or improved in vitro metabolic profiles in whole blood, with 5-PMFC being clearly the most superior. This study has identified a particularly advantageous structural moiety (aryl ether) that can be manipulated to further improve on pharmacologic profiles, both in terms of potency and improved resistance to metabolism.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A prodrug or protected form of 5-hydoxymethyl-2-furfural (5-HMF) with a generic formula:

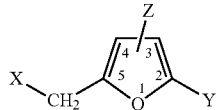

Formula I where:

X is $R_{12}$—O—· where $R_{12}$ is alkyl or aryl, and the bond marked with * bonds directly to $CH_2$ of Formula I;

Y is

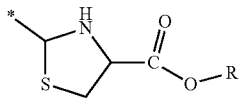

where R is alkyl, and where the bond marked with * bonds directly to carbon at position 2 of the furan ring of Formula I;

and

Z is H, OH, alkyl, aryl, O-alkyl, O-aryl or O-heteroaryl.

2. A method of treating or prophylactically treating sickle cell disease in a subject in need thereof, comprising administering to the subject a therapeutically effective amount of a prodrug or protected form of 5-hydoxymethyl-2-furfural (5-HMF) with a generic formula:

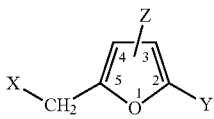

Formula I where:

X is $R_{12}$—O—· where $R_{12}$ is alkyl or aryl, and the bond marked with * bonds directly to $CH_2$ of Formula I;

Y is

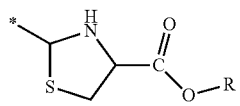

where R is alkyl, and where the bond marked with * bonds directly to carbon at position 2 of the furan ring of Formula I;

and

Z is H, OH, alkyl, aryl, O-alkyl, O-aryl or O-heteroaryl.

3. A method of treating or prophylactically treating hypoxia in a subject in need thereof, comprising administering to the subject a therapeutically effective amount of a prodrug or protected form of 5-hydoxymethyl-2-furfural (5-HMF) with a generic formula:

Formula I where:

X is $R_{12}$—O—· where $R_{12}$ is alkyl or aryl, and the bond marked with * bonds directly to $CH_2$ of Formula I Y is where R is alkyl, and where the bond marked with * bonds directly to carbon at position 2 of the furan ring of Formula I;

and

Z is H, OH, alkyl, aryl, O-alkyl, O-aryl or O-heteroaryl.

4. The prodrug or protected form of 5-hydroxymethyl-2-furfural (5-HMF) having the structure

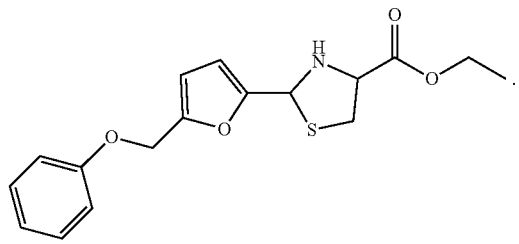 [SMILES: CCOC(=O)C1CSC(c2ccc(COc3ccccc3)o2)N1]

* * * * *